United States Patent [19]
Heilman et al.

[11] Patent Number: 5,980,448
[45] Date of Patent: Nov. 9, 1999

[54] SINGLE CHAMBER BLOOD PUMP

[75] Inventors: Marlin Stephen Heilman, Sarver; Christopher David Capone, Pittsburgh; Edward Karl Prem, Allison Park; Richard Andrew Zehel Sofranko, Pittsburgh; Carl Michael Parisi, Kittanning; Steve Andrew Kolenik, Leechburg; Daniel Richard Moore, Pittsburgh, all of Pa.

[73] Assignee: Vascor, Inc., Pittsburgh, Pa.

[21] Appl. No.: 09/014,894

[22] Filed: Jan. 28, 1998

[51] Int. Cl.[6] ................................................ A61M 1/12
[52] U.S. Cl. .................................................. 600/16; 623/3
[58] Field of Search ............................ 600/16, 17; 623/3

[56] References Cited

U.S. PATENT DOCUMENTS

| | | |
|---|---|---|
| 3,553,736 | 1/1971 | Kantrowitz et al. . |
| 3,692,018 | 9/1972 | Goetz et al. . |
| 4,034,742 | 7/1977 | Thoma . |
| 4,051,840 | 10/1977 | Kantrowitz et al. . |
| 4,091,471 | 5/1978 | Richter . |
| 4,104,005 | 8/1978 | Poirier . |
| 4,167,046 | 9/1979 | Portner et al. ............................ 623/3 |
| 4,195,623 | 4/1980 | Zeff et al. . |
| 4,250,872 | 2/1981 | Tamari . |
| 4,630,597 | 12/1986 | Kantrowitz et al. . |
| 4,733,652 | 3/1988 | Kantrowitz et al. . |
| 4,938,766 | 7/1990 | Jarvik . |
| 5,089,016 | 2/1992 | Millner et al. . |
| 5,133,742 | 7/1992 | Pinchuk . |
| 5,263,978 | 11/1993 | Kaufmann et al. ......................... 623/3 |
| 5,282,849 | 2/1994 | Kolff et al. . |
| 5,314,469 | 5/1994 | Gao ........................................... 623/3 |
| 5,569,156 | 10/1996 | Mussivand . |
| 5,599,173 | 2/1997 | Chen et al. . |

FOREIGN PATENT DOCUMENTS

WO 95/07109  3/1995  WIPO .

*Primary Examiner*—William E. Kamm
*Assistant Examiner*—George R. Evanisko
*Attorney, Agent, or Firm*—Buchanan Ingersoll, P.C.

[57] ABSTRACT

A blood pump apparatus can include a pump housing having a drive chamber containing a drive mechanism. A cupped member can be connected to the housing and the drive mechanism can include a motor for rotating an eccentric shaft. A pumping arm can be provided having one end riding on the eccentric shaft, an intermediate portion pivotably attached to the housing and another end connected to a movable plate. A roller bearing can be mounted on the eccentric shaft on which the arm can ride. A compressible blood chamber having an inlet and an outlet connected can be provided sandwiched between the cupped portion and the movable plate. The motor thus rotates the cam causing the pumping arm to pivot which cycles the movable plate against the blood chamber to pump blood. The movable plate can be implanted adjacent a lung such that the lung moves with the plate as blood is pumped and thereby functions as a compliance chamber. A speed reducer can be provided between the motor and the eccentric shaft. A hermetically sealing bellows can be provided to seal the drive chamber and the end of the pumping arm from body fluids. An enclosure bag can be provided surrounding all or a portion of the blood pump to provide a tissue friendly surface and to prevent tissue from becoming caught in the moving parts of the blood pump. A position sensor can be included for determining a volume of blood in the chamber for use by an electronic controller to control the speed of the motor to optimize pumping action.

56 Claims, 15 Drawing Sheets

FIG.12a
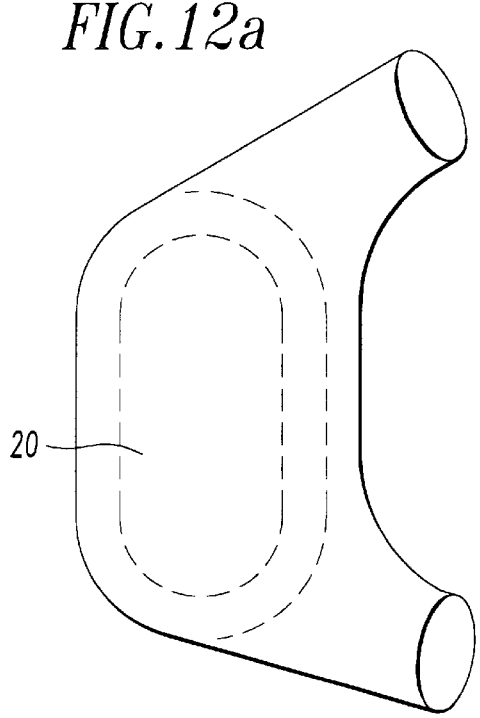
FIG.12b
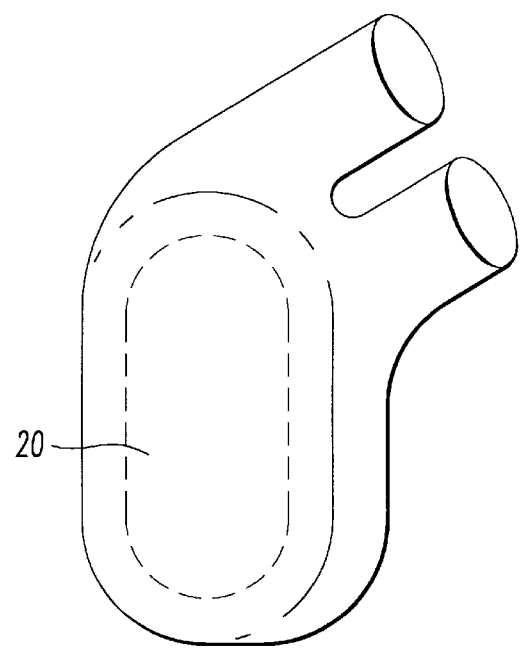
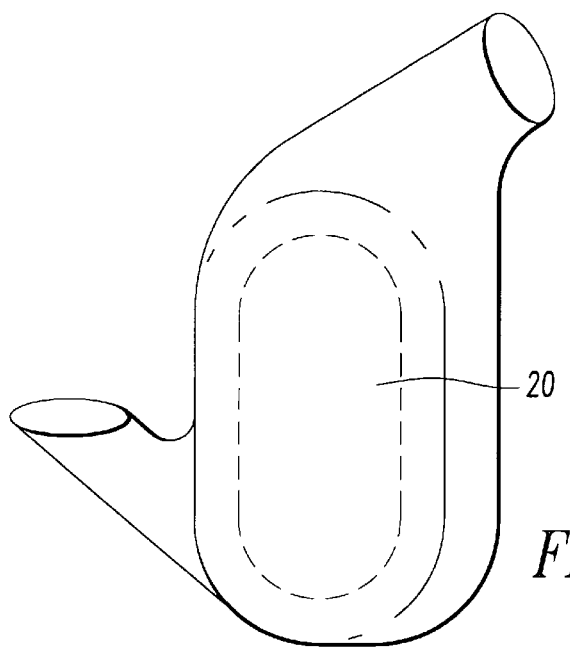
FIG.12c

SINGLE CHAMBER BLOOD PUMP

BACKGROUND

The invention relates generally to implantable blood pumps, and particularly to a fully implantable single chamber blood pump apparatus.

Serious heart failure, or the inability of a person's heart to pump sufficient blood for their body's needs, is the cause of very poor quality of life, huge medical treatment costs, and death in hundreds of thousands of patients yearly. Numerous pharmacologic, biologic, and device interventions have been devised to deal with this disease, many of them patented, but despite these efforts, heart failure remains a major public health problem.

The measure of heart failure is an abnormally low cardiac output or cardiac index. Cardiac output (CO) is measured in liters of blood flow per minute (1/min) and cardiac index (CI) is CO divided by the patient's body surface area (BSA). Normally CI at rest or during light activity is between 3.0 and 3.5 and CO is between 5.6 to 6.5 liters per minute for men and proportionally less for women based upon less body surface area. Severe heart failure exists when the CI is between 1.5 and 2.0. For an average man in heart failure with 1.87 meters squared BSA, a cardiac index of 1.75 and a heart rate of 80 beats per minute (BPM), the cardiac output will be 3.27 l/min and an average of 41 ml of blood will be ejected from the heart with each heartbeat. This average stroke volume contrasts with an average normal stroke volume of 76 ml, which would occur in an average normal man with a CI of 3.25 and heart rate of 80 BPM. The main pumping chamber of the heart or left ventricle (LV), has an inlet (mitral) valve and an outlet (aortic) valve. During left ventricluar contraction, the inlet valve closes as blood is pushed through the aortic valve and into the aorta or main artery of the body. Resting (diastolic) LV pressure may be between 2 and 20 mm Hg pressure (preload) and will be in the higher end of this range during failure. During active LV contraction (systole), the LV must eject the blood against aortic pressure, which is typically between 70 and 140 mm Hg of pressure (afterload). It is well known that, if in failure the afterload is reduced, the stroke volume will naturally increase and this increase is one reason that afterload-reducing drugs such as ACE-inhibitors have helped heart failure patients.

A common method of providing mechanical circulatory assist is the use of counterpulsation devices such as intraaortic balloon pumps (IABPs). IABPs provide an afterload-reducing type of assist and are typically employed for acute use (i.e. for hours to days). As described in U.S. Pat. Nos. 4,733,652 and 3,692,018 to Kantrowitz et al. and Goetz et al., respectively, the main benefit of such devices stems from unloading the left ventricle during systole and providing increased diastolic pressure for reperfusing the coronary and other arteries during diastole. Patients needing this type of treatment suffer from cardiogenic shock, chronic angina, or need perioperative circulatory support (Nanas et al. 1988, Kormos 1987). The nature of IABP design restricts itself to acute use only, since the bulky balloon drive unit remains outside the patient's body necessitating confinement to a hospital bed.

Pouch-type auxiliary ventricles that have mechanical or pneumatic means for the pumping the contained blood are disclosed in U.S. Pat. Nos. 3,553,736 and 4,034,742 to Kantrowitz et al. and Thoma, respectively. Many of these have a single access port that serves as both the inlet and the outlet for bloodflow. These designs have the disadvantage of relative flow stagnation which increases the risk of clot formation and thromboembolism. Others have both an inlet and outlet port and can be connected in parallel with the aorta. These designs may have valves to attempt to maximize their pumping effectiveness (U.S. Pat. Nos. 4,195,623 and 4,245,622 to Zeff et al. and Hutchins, respectively.)

A "dynamic aortic patch" is disclosed in U.S. Pat. Nos. 4,630,596 and 4,051,840, both to Kantrowitz et al., which is permanently attached to the aorta and is designed to provide counterpulsation assistance. This device is intended for chronic use and requires opening the patient's thorax for installation. Like the IABP, the drive unit remains outside the patient's body and inflation of the patch is accomplished pneumatically through a percutaneous access port. Unlike the IABP, the dynamic aortic patch can produce volumetric assistance greater than 40 ml. Two risks of this system are the risk of chronic infection due to the permanent percutaneous port and the extensiveness of the implant surgery. Physically, the patch is oblong in shape and consists of a flexible balloon on the blood side of a chamber that has a rigid back through which a pneumatic line (hose) passes to effect balloon inflation and deflation. Along the perimeter of the rigid back is a flange that provides an edge for suturing the patch into the aortic wall. The hose penetrates the skin surface percutaneously through a specially designed skin port. Inflation and deflation of the balloon is accomplished by an external air pump that is connected to the intraaortic patch during operation. When and if the balloon is not being pulse driven, the aorta is open to bloodflow allowing the pump to be fail-safe. In the standby mode, the balloon interior is then at atmospheric pressure which is lower than aortic blood pressure causing the pumping chamber to collapse.

The addition of compliance to the arterial system is described in U.S. Pat. No. 4,938,766 to Jarvik. Hardening of the arteries lowers vascular compliance and can increase the afterload presented to the heart. Consequently, the addition of a compliance chamber can help to somewhat reverse the effects of arterial hardening and hence decreases the heart's workload. From the disclosure, such devices are generally used to assist the left ventricle. Several configurations of compliance chambers are disclosed and various methods of implantation are also taught. The devices can be categorized as single-port chambers, two-port flow-though chambers, and spring-loaded mechanical clips that are attached to the aorta. For designs having a flow-through configuration, a valve may be included in the inlet side of the chamber. This can be for preventing backflow and preferentially can direct the outflow of blood from the compliance chamber towards more desired locations.

Direct pumping during heart diastole is typically performed by what are referred to as ventricular assist devices (VADs). VADs that have a flow-through configuration and which convert electric energy directly to mechanical energy are the most pertinent prior art to the invention described herein. U.S. Pat. No. 4,091,471 to Richter describes an apparatus that mechanically compresses a toroidal flow conduit by squeezing the inner radius and pushing it outward while preventing the outer radius from expanding. This is accomplished through pressurization of a sealed central portion, in the center of the toroid. U.S. Pat. No. 4,250,872 to Tamari describes a flow-through pumping chamber which is squeezed by a pressurizing fluid. The Tamari device relies mainly on thickness variations of the pumping chamber wall to control compression of the pumping chamber. U.S. Pat. No. 5,089,016 to Millner et al. has a flow-through toroidal design which employs a hydraulic pumping fluid to compress the pumping toroidal chamber. The Millner device can have valves at both the inlet and the outlet of the pumping chamber. The pumping chamber itself is squeezed from all directions circumferentially to accomplish blood pumping. However, to minimize wall stress in the pumping chamber, the chamber can preferably be squeezed in one direction by stiffening the opposite side of the chamber wall.

Articles published by Frazier et al. (*Circulation*, 89:2908–2914, 1994) and McCarthy et al. (*Ann Thoracic Surg*, 59:S46–S51, 1995) describe a blood pump which has a diaphragm-driven circular chamber that is implanted in the upper left abdominal wall and is capable of an 83 ml stroke volume. The pumping chamber receives blood from a conduit that pierces the apex of the LV. The pumping diaphragm may be driven pneumatically or by an electric motor driving a single rotation roller-cam mechanism. In both cases, the pumping chamber is circular and drive lines pierce the skin. Adequate filling of the chamber is possible because the nonblood side of the drive membrane is vented to the atmosphere via the skin port.

The blood pump disclosed in U.S. Pat. No. 5,569,156 to Mussivand has the nonblood side of the drive membrane contacting hydraulic fluid that, during filling, must be actively pumped to a separate volume displacement chamber (VDC). The blood pump also has inlet and outlet ports that are perpendicular to the blood pumps drive membrane.

The blood pump disclosed in an article by Ramasamy et al. (*ASAIO Transactions*, 35:402–404, 1989) illustrates a separate gas filled compliance chamber placed in the pleural space that communicates by means of gas tight tubing to the nonblood contacting side of the blood chambers pumping membrane.

For ease of filling, it is necessary for the non-blood-contacting side of the diaphragm to be at or near atmospheric pressure to permit easy blood inflow. Artificial VAD pumping chambers, together with their associated electronics and drive mechanisms, are not yet sufficiently compact to be fully implanted. Instead, various leads have to penetrate the skin and connect the pumping chamber with the external drive mechanism. To permit easy filling of the pumping chamber with blood, a low opposing pressure is needed. The preceding articles describe three means for accomplishing this low pressure; venting through the skin to atmospheric pressure, venting to a separate gas filled compliance chamber in the pleural space, and using an intermediate hydraulic fluid connected to an implanted volume displacement chamber or VDC.

The pumping chamber described in Frazier et al. has a bloodflow path which is parallel to the LV since the chamber receives blood from the LV apex and pumps the blood into the aorta beyond with a flow path in parallel with the LV.

Accordingly, there is a need for a blood pump which is small enough that, together with its associated electronics, can be totally implanted to avoid the infection risk associated with percutaneous leads. The blood pump also should not require a second chamber for compliance, whether in the form of a chamber which is a part of the pump or a separately located chamber connected to the pump with gas tight tubing. Moreover, in contrast to the parallel connection pathway, it can be preferable to have a blood pump which receives blood from the aortic root at a low filling pressure and return the blood to the ascending aorta by driving the pump and blood to a higher pressure than exists in the distal aorta. Such a connection configuration would be referred to as "in-series" with the left ventricle.

SUMMARY

An implantable blood pump apparatus according to the invention can include a pump housing having a pump portion and a drive chamber containing a drive mechanism. The pump portion can be a flat or cupped shaped plate member that can be connected to the housing. The drive mechanism can include an electric servo-motor having a stator, a rotor and an output shaft. The output shaft can be connected to an eccentric shaft that can have a cam portion. The cam can be a roller cam and a pumping arm can be provided having one end following the cam and an intermediate portion of the pumping arm can be pivotably attached to the housing. The end of the pivoting arm has intermittent contact with a cam surface such that a surface of the pumping arm end acts as the cam follower. An opposite end of the pumping arm can be connected to a movable plate. A compressible blood chamber, having an inlet and an outlet connected to a circulatory system, can be provided sandwiched between the cupped portion and the movable plate. A valve can be provided at the outlet of the blood chamber to help ensure that the arterial blood passes through the blood chamber in only one direction. The motor thus can rotate the cam which causes the pumping arm to pivot about the rotation center, i.e. the fixed intermediate portion. The pivoting motion of the pumping arm operates the movable plate to cyclically compress and release the blood chamber and pump blood through the circulatory system. Preferably, the movable plate side of the blood pump apparatus can be implanted adjacent to a lung such that as the movable plate moves the lung moves with the movable plate as blood is pumped. The lung can thereby be utilized as a compliance chamber for the blood pump apparatus. Consequently, a separate compliance chamber need not be provided. Preferably, a speed reducer can be provided connected between the output of the servo motor and the eccentric shaft. The speed reducer can be a planetary gear arrangement which can have four planets. Additionally, a hermetically sealing metal bellows member can be provided around the drive chamber and the intermediate portion of the pumping arm. The bellows member can seal off the drive chamber around the end of the pumping arm to prevent body fluids from contacting the drive mechanism. The metal bellows provides the means for both hermetically sealing the space and for transmitting motion from the drive assembly without breaking hermeticity.

A polymeric enclosure bag, preferably filled with isotonic saline solution, can surround all or only a part of the blood pump apparatus to provide a tissue friendly surface for surrounding tissue. The enclosure bag can also prevent the tissue from getting caught in the moving parts of the blood pump apparatus. A position sensor can also be provided for determining a relative volume of blood in the blood chamber. The position sensor can be located adjacent the intermediate portion of the pumping arm for detecting angular changes in the pumping arm as it pivots. This information can be indicative of both the volume of blood in the blood chamber and of the cam position. Such information can be employed to control the speed of the motor in order to optimize the pumping action, especially regarding when expulsion of the blood from the blood chamber should be initiated.

The blood pump apparatus can be implanted in various configurations. Standard vascular grafts can used for the inlet and outlet. The outlet cannula can be connected to the ascending thoracic aorta. The inlet cannula may either be connected to the ascending thoracic aorta (in series) and can have only one valve in the outlet cannula or the inlet cannula may be connected to the left ventricular (IV) apex (in parallel) in which case both the inlet and outlet cannulae can have integral valves.

A hermetically sealed electronic controller can also be implanted to provide several functions for controlling the operation of the blood pump apparatus. ECG leads can be connected to the heart which supply signals to the electronic controller. Such signals can be used to control pacing and, additionally, on demand defibrillation. The same leads can be used to pace the patient's heart if needed. Since many heart failure patients can have a high risk of ventricular fibrillation (sudden cardiac death), cardioversion/defibrillation leads can also be provided emanating from the electronic controller. Electrical energy can supplied to the electronic controller via a transcutaneous energy and data transmission system (TEDTS). The TEDTS can utilize an encapsulated, subcutaneous (secondary) coil which in turn connects to the electronic controller. A mating external (primary) coil can be secured to the patient's skin to electromagnetically transmit energy to the internal coil to power the implanted system. The coil combination can also be used to bidirectionally transfer data between the implanted system and external sensing and programming devices. One such system for transmitting power and data through the skin is described by Prem et al. in U.S. Pat. No. 5,630,836. Internal batteries can be charged during normal TEDTS operation. If the external TEDTS coil is removed from the patient's skin or if the TEDTS is otherwise powered down, the implanted battery pack can provide the power needed for several hours of implanted system operation.

Other details, objects, and advantages of the invention will become apparent from the following detailed description and the accompanying drawing figures of certain embodiments thereof.

BRIEF DESCRIPTION OF THE DRAWINGS

A more complete understanding of the invention can be obtained by considering the following detailed description in conjunction with the accompanying drawings, wherein:

FIGS. 12a–12c are side views of different polymeric blood chamber configurations;

DETAILED DESCRIPTION CERTAIN EMBODIMENTS

Figure 1:
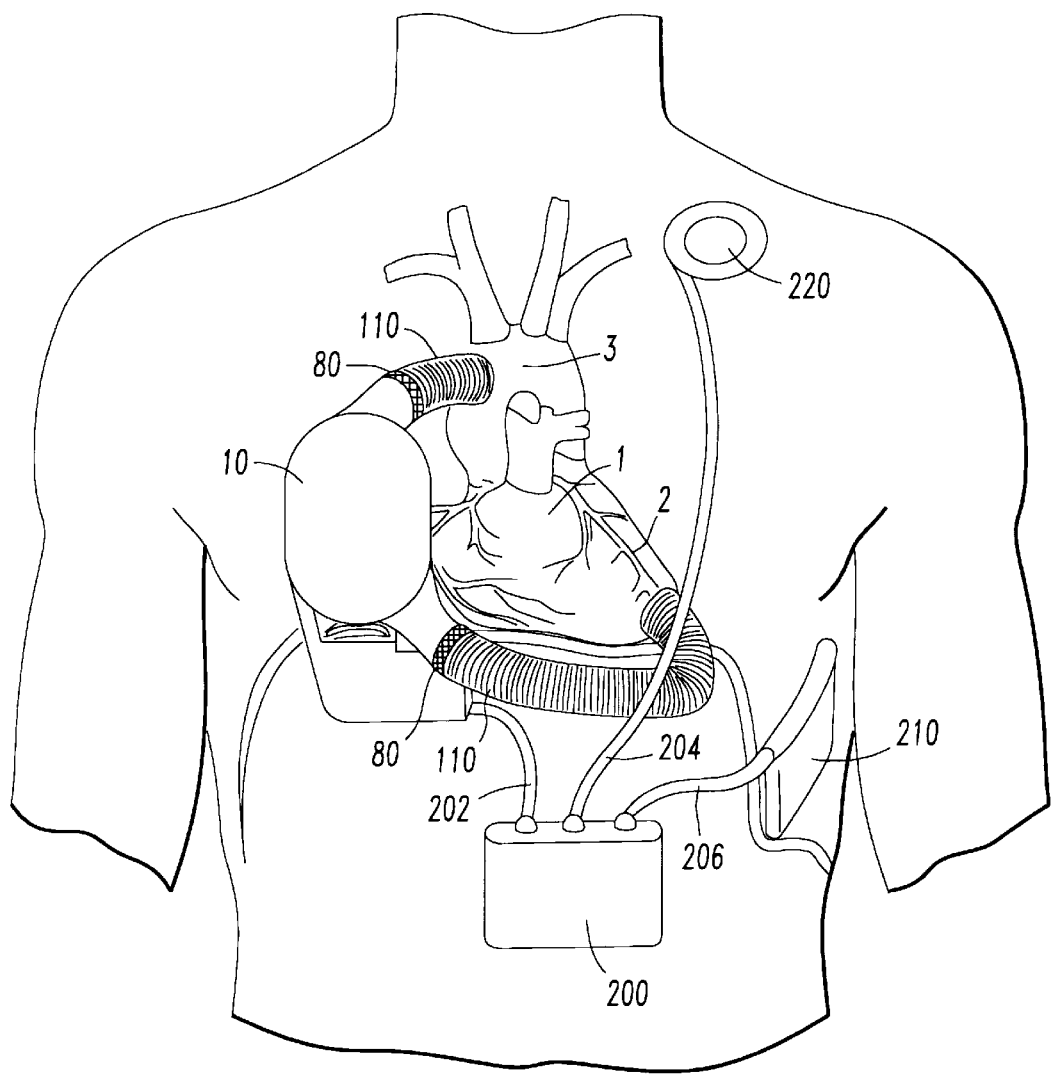
FIG. 1 shows an in-parallel connected blood pump in the right thorax.

Referring now to the drawing figures wherein like reference numbers refer to similar parts throughout the several views, a fully implantable blood pump apparatus is shown in FIGS. 1–7 operatively connected to a patients circulatory system along with certain associated components, such as an electronic controller (EC) 200, a battery pack 210 and a TEDT 220.

Figure 4:
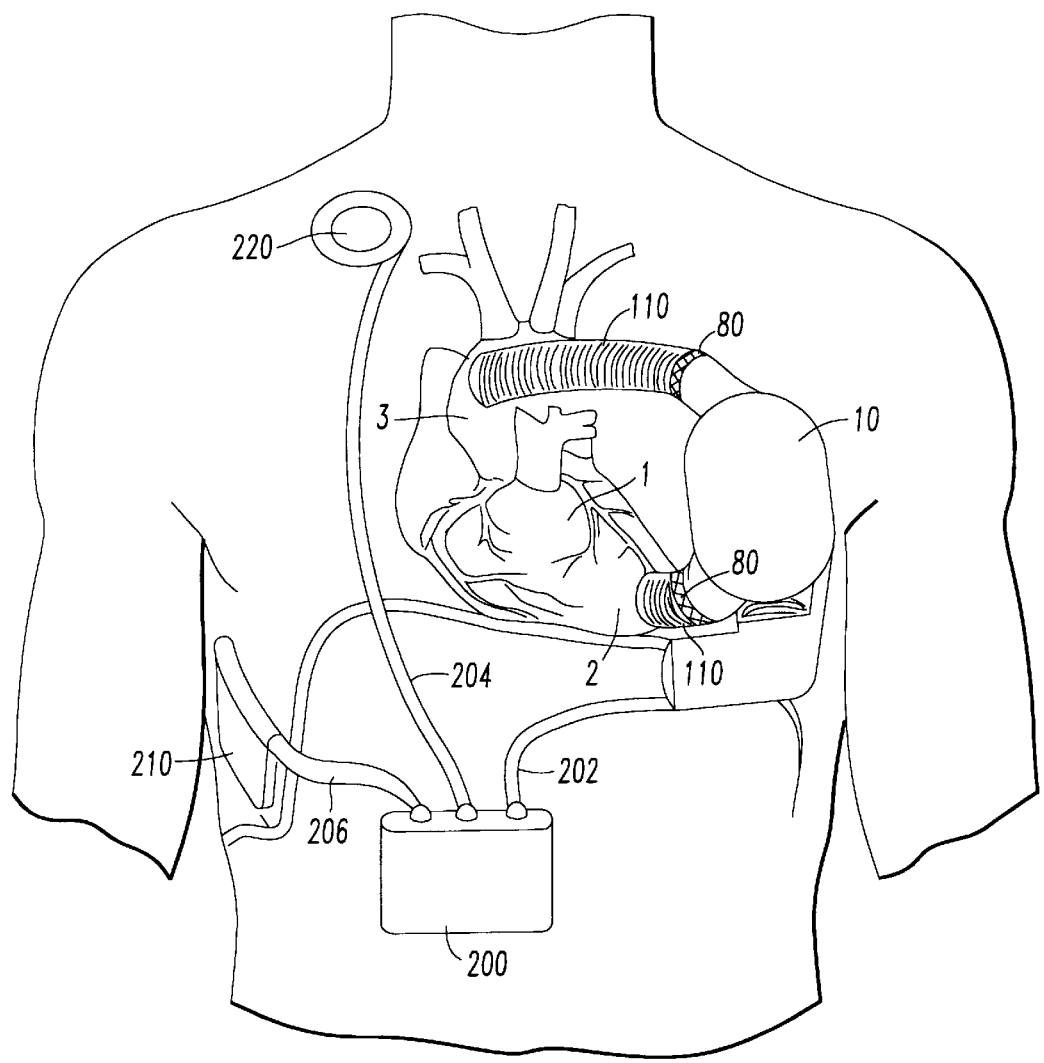
FIG. 4 shows an in-parallel connected blood pump in the left thorax.
Figure 5:
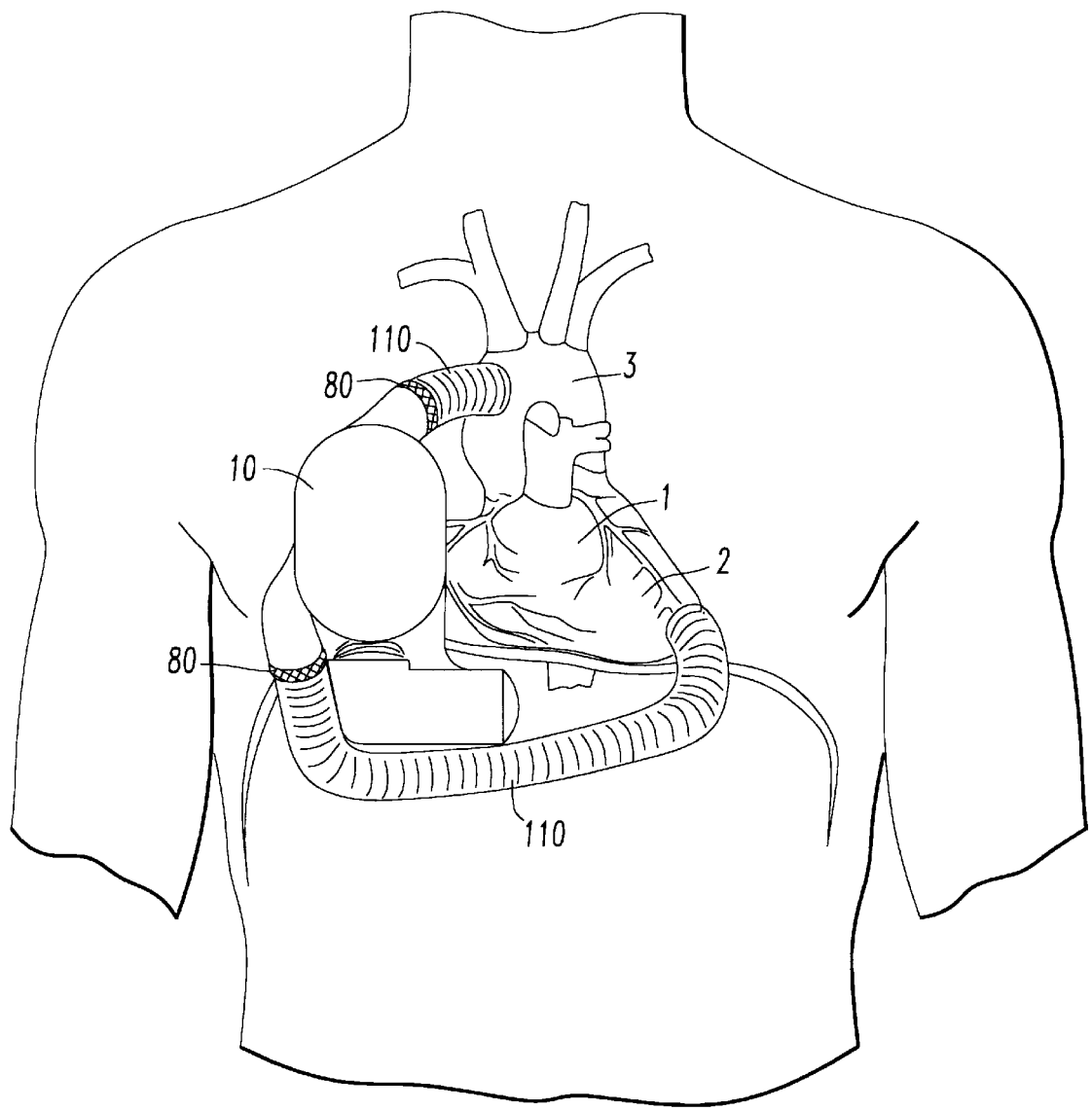
FIG. 5 shows an alternate in-parallel connected blood pump in the right thorax.

The blood pump apparatus 10 can be implanted in either the right or left chest and can be connected to the circulatory system either in-parallel or in-series. Alternate right chest implant configurations for in-parallel ventricular assist are shown in FIGS. 1 and 5. A left chest implant configuration for in-parallel ventricular assist is shown in FIG. 4. In either right or left chest implantation, the blood pump 10 can be implanted in the human thorax with the bloodflow path from the LV apex to the ascending aorta. The blood pump 10 can be positioned such that the lung is slightly pushing against the moving side of the pump. This placement can result in the pump being auto-compliant by using the lung tissue to obviate the need for a separate compliance chamber. The pumping function is also more directly in line with the bloodflow conduits.

Figure 2A:
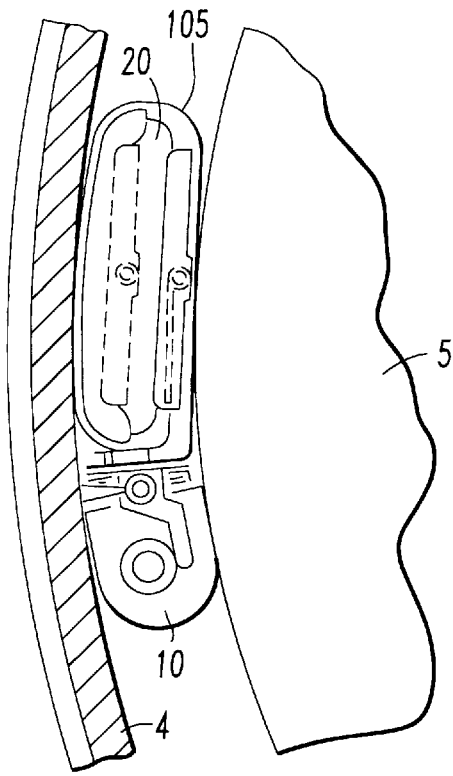
FIGS. 2a is an axial section view of the blood pump in FIG. 1 position between a patient's ribcage and lung.
Figure 2B:
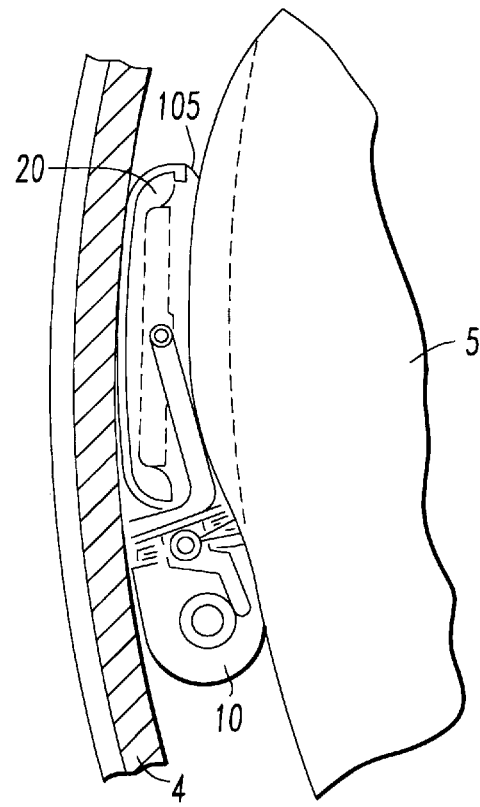
FIG. 2b is the blood pump in FIG. 2a illustrating how the lung can act as a compliance chamber for the pump.

In any configuration, the blood pump 10 can be placed against the inside of the chest wall at a height approximately the same as the heart, as shown in FIGS. 2a and 2b. It can be observed that as the blood pump 10 squeezes the blood chamber 20, the blood pump 20 becomes thinner by the volume of ejected blood. Expanding lung tissue fills the space created by the collapsing pump. The lung thus acts as a compliance chamber for the blood pump 10. This can be a distinct advantage over conventional blood pump assemblies which require an artificial gas filled chamber for compliance. Over time the artificial chamber can lose gas volume due to diffusion. Consequently, it can be necessary to periodically refill the chamber to maintain the filling ability of the blood pump assembly. In most conventional systems, the blood pump assembly is too large to fit in the thorax. In these systems, the compliance chamber may be an entirely separate component from the blood pump assembly, which may be implanted at a different location wherever space is available. Gas tight tubular connections can then be provided to connect the compliance chamber to the blood pump assembly. Consequently, an auto-compliant blood pump apparatus can have few implanted components and can require less space for implantation. The present invention can therefore be substantially more space efficient than prior art blood pump assemblies which require a separate compliance chamber.

Figure 3:
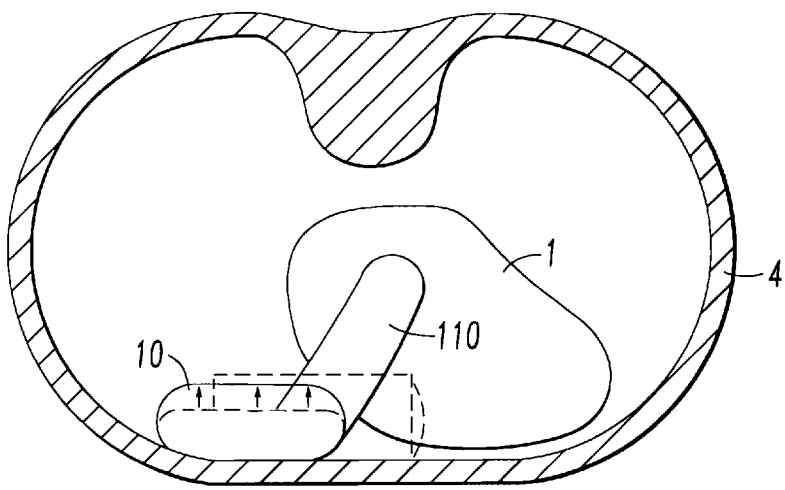
FIG. 3 shows a sagittal view of the blood pump in FIG. 1.

The use of the intrathoracic lung space for compliance can have many advantages. For example, since the pressure in this space is very close to atmospheric pressure, it provides ideal conditions for filling of the pumping chamber while eliminating the need for a compliance chamber. Additionally, for obvious reasons, the fewer components which require implantation in the body the better. Moreover, the lungs are very compliant and can tolerate a slight compression and expansion generally without damage or loss in lung function. Also, unlike artificial compliance chambers, the lungs don't "leak" and thus do not require periodic refilling. Further, the ribcage offers protection for the blood pump. The blood pump can be situated on the inside of the thoracic wall against the ribs adjacent to the heart, as shown in FIG. 3. The generally flat form of the pumping chamber allows a minimum amount of interference with lung function as well as efficiently using the occupied space.

Figure 6:
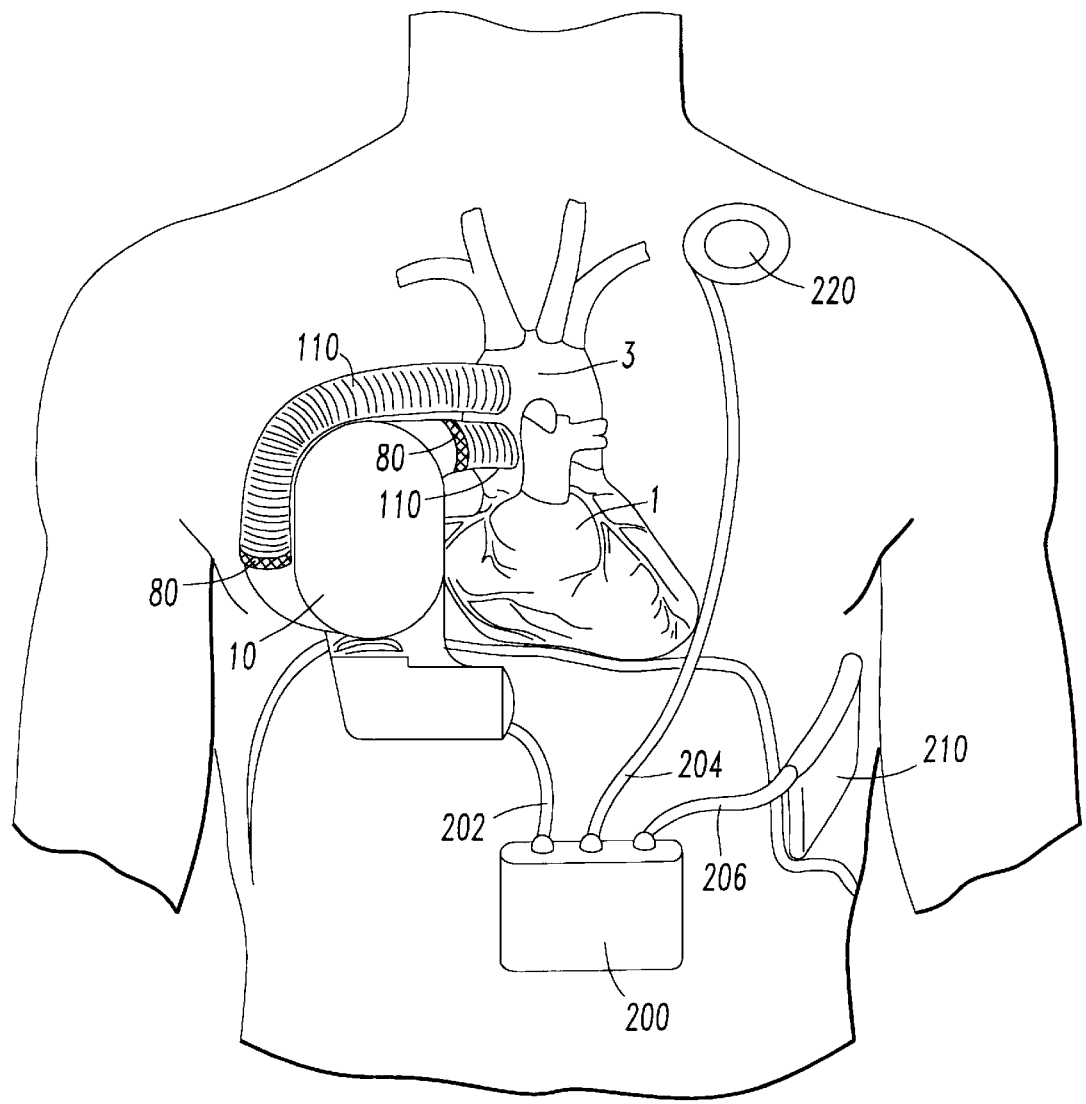
FIG. 6 shows an in-series connected blood pump in the left thorax.
Figure 7:
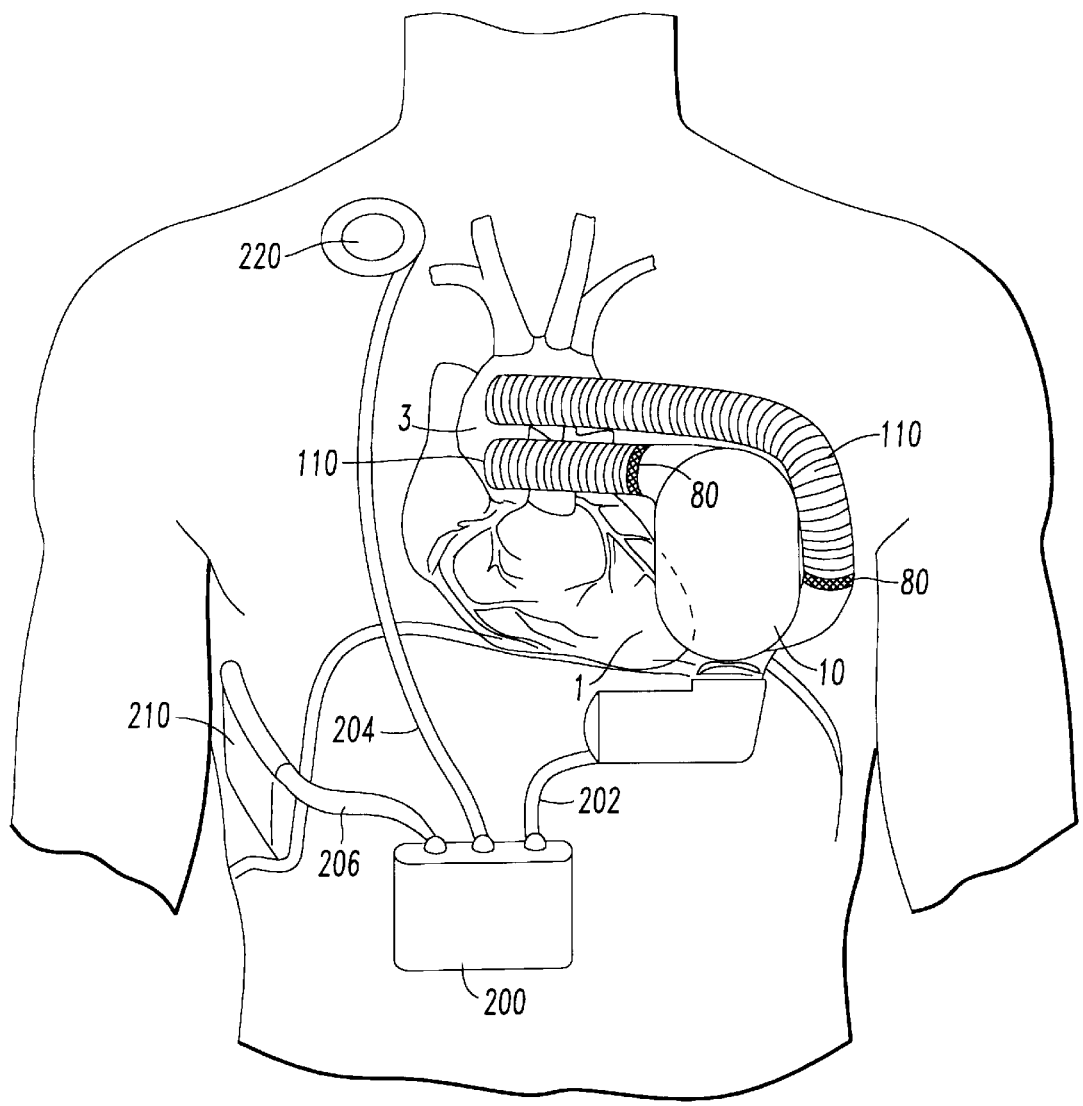
FIG. 7 shows an in-series connected blood pump in the right thorax.

The blood pump 10 can also be attached to the circulatory system in an in-series configuration, as shown in FIGS. 6 and 7. Conventional VADs can typically be attached to the circulatory system in the in-parallel configuration, shown in FIGS. 1, 4 and 5 wherein the inlet conduit receives blood from the left ventricular apex 2. In that arrangement, the blood flows from the bottom of the ventricle into the pump. The conventional VAD blood path is in parallel with the normal LV bloodflow path. Thus, if the conventional VAD pump fails, this parallel leg can be likely to clot due to blood stagnation. With the in-series configuration, failure of the pump may impose a longer than normal bloodflow path, but the blood can still pass through the pump and therefore clotting and thrombi can be less likely. The in-series configuration can therefore be safer compared to the in-parallel configuration in the event of pump failure. Not only can the risk of blood flow stagnation in the pump be reduced with pump failure in the in-series configuration, but the risk of bloodflow stagnation high in the LV can also be reduced because the blood coming from the LV comes as it does normally through the aortic valve instead of out the LV apex as occurs in the in-parallel configuration. Another advantage of the in-series configuration is that only one valve, in the pump outlet conduit, can be required. In contrast, the parallel configuration can require two valves, one for each of the inlet and outlet conduits. The valves may either be within the length of the conduits or the valve may be part of the connector assembly. In either instance, a mechanical or bioprosthetic valve may be used. The serially connected pump, however, can require only a single valve located in the outlet graft, since the natural aortic valve of the heart can serve as the inlet valve for the blood pump.

Conventional techniques for attaching the conduits to the circulatory system are illustrated in FIGS. 8a–9c. The conduit to blood pump connections may be completed by suturing, using spool-type connections or using premanufactured quick connectors. The spool-connectors are designed to have vascular grafts slipped over them and be fastened to the spools with a band or ligature. The quick-connectors have mating ends for connecting the conduit to the blood pump. The ends of the blood chamber 20 and the ends of the enclosing polyurethane sack terminate at these connection points regardless of the type of connection used.

Figure 8A:
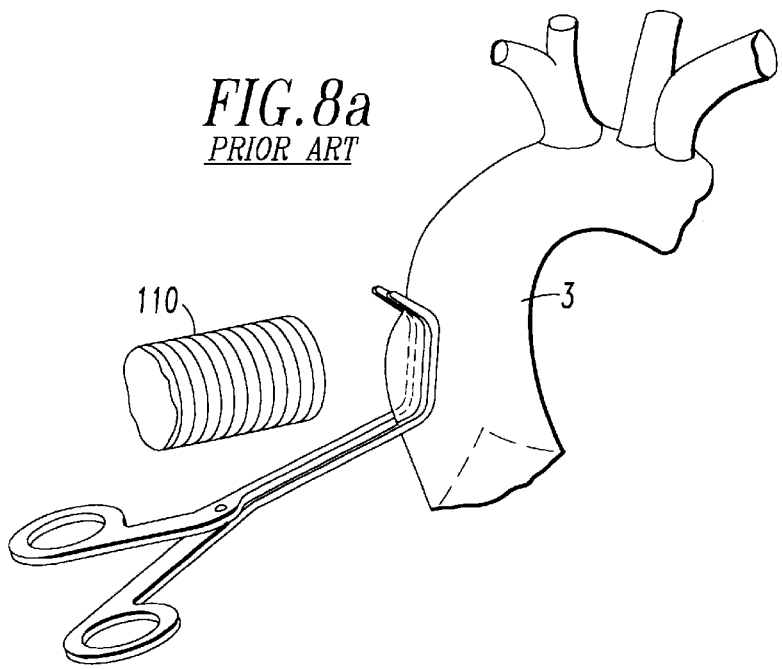
FIGS. 8a–8c show an aortic graft installation.
Figure 8B:
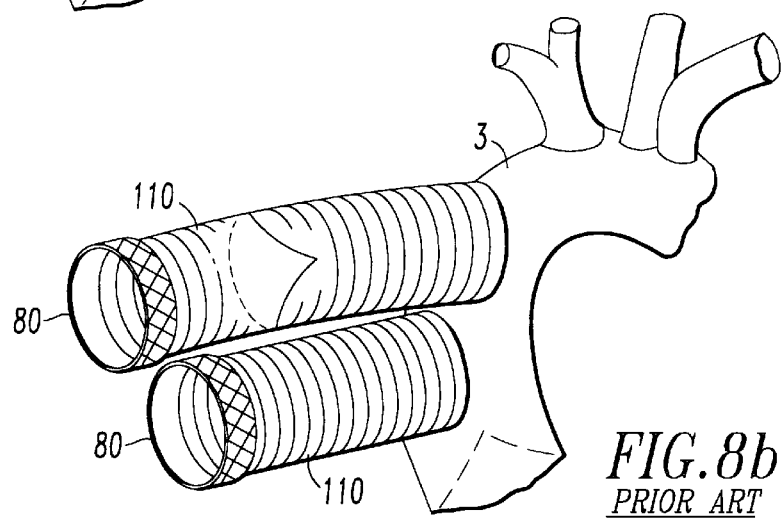
Figure 8C:
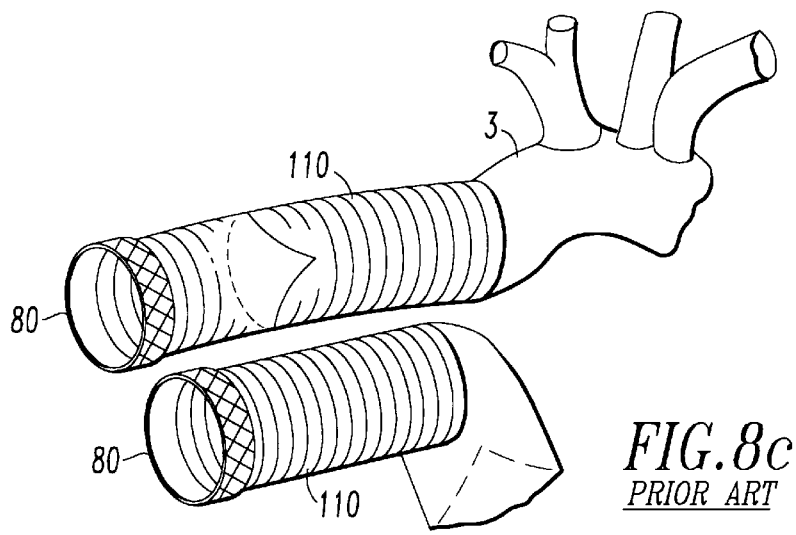

An in-series implantation technique is depicted in FIGS. 8a–8c wherein a segment of the ascending thoracic aorta is first exposed for connecting to the inflow conduit. Satinski clamps are used to pinch off a segment of aortic wall while normal aortic flow remains uninterrupted. Longitudinal incisions are made in the clamped-off portions of the aorta in preparation for graft installation. Vascular grafts are then sewn to the aorta using surgical sutures in an end-to-side connection. The proximal clamp is released first and air is bled from the cannulae using a hypodermic needle. After the air has been evacuated, the distal clamp is released. A separation or coarctation of the aorta is then created in the ascending aorta to enable serial flow from the LV through the blood pump into the arterial system. End-to-end anastomoses can also be used with heart bypass to connect the in-series conduits to the aorta.

Figure 9A:
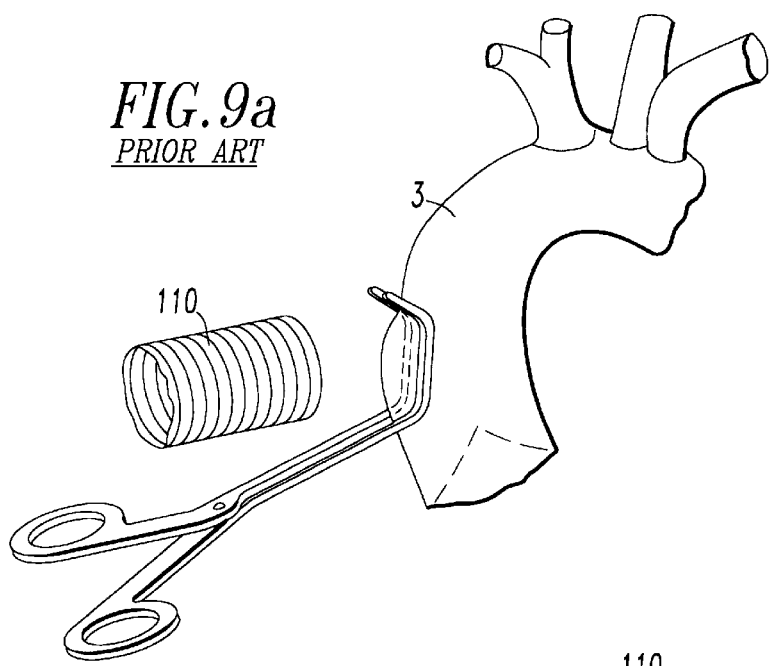
FIGS. 9a–9c show an aortic graft and an LV apical graft installation.
Figure 9B:
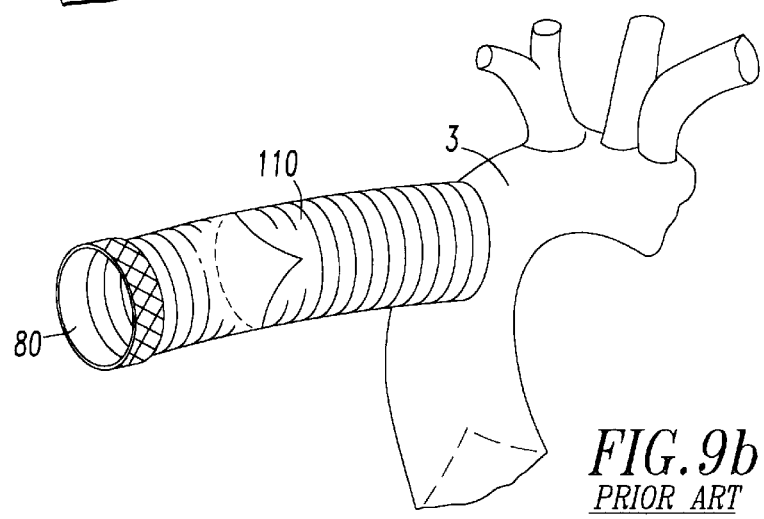
Figure 9C:
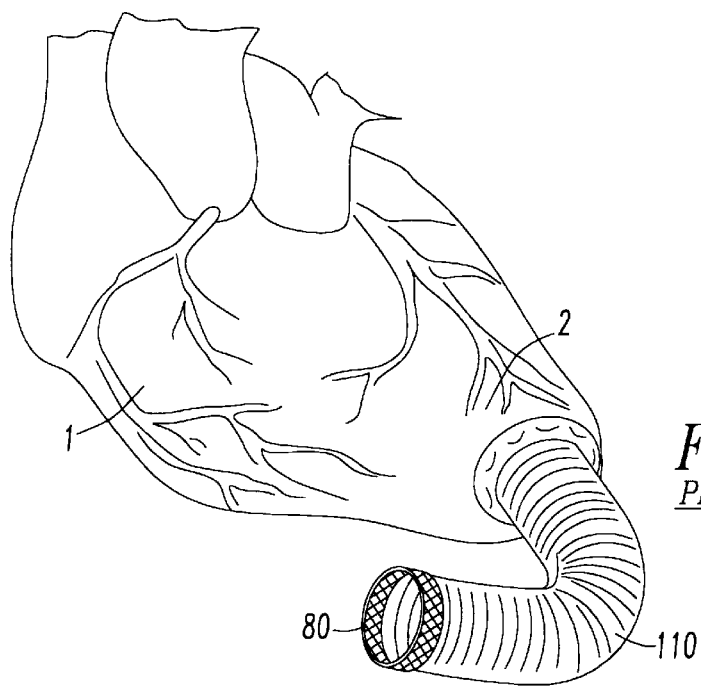

An in-parallel implantation technique is depicted in FIGS. 9a–9c wherein a segment of the ascending thoracic aorta is first exposed for cannula installation. A Satinski clamp is used to pinch off a segment of aortic wall while normal aortic flow remains uninterrupted. A longitudinal incision is made in the clamped-off portion of the aorta in preparation for graft installation. A vascular graft is then sewn to the aorta using surgical sutures in an end-to-side fashion. This graft will then be used for the outlet conduit of the blood pump. A cannula is then installed in the LV apex and connected to the inlet conduit of the blood pump. The parallel connected blood pump will probably need heart bypass for implantation due to the air embolism risk from having the opening in the LV apex.

Figure 10:
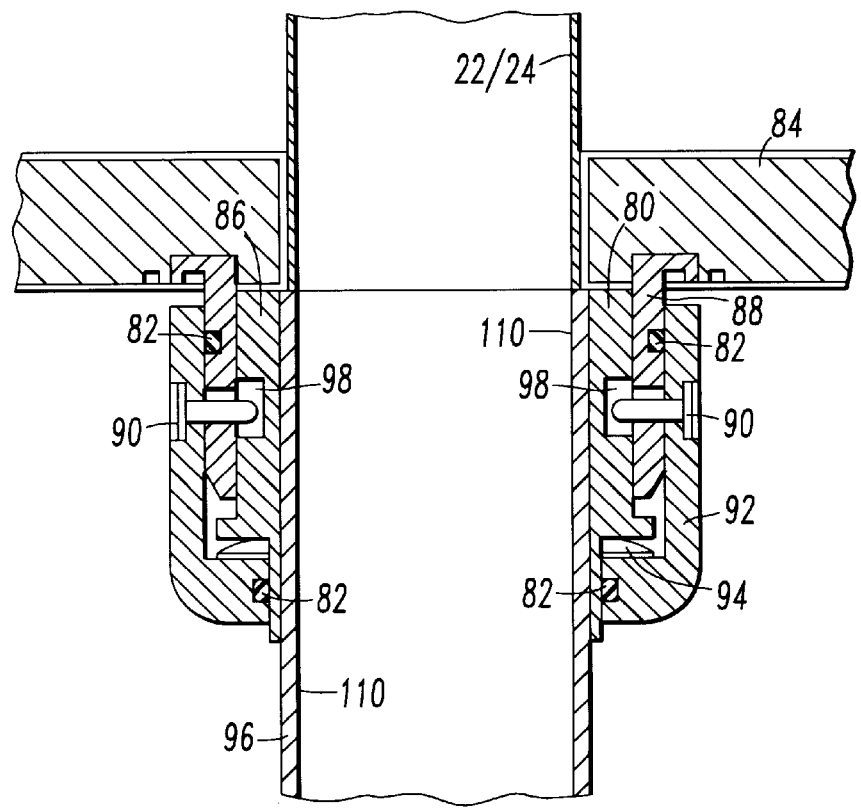
FIG. 10 is a side sectional view of a quick connector and cannula.
Figure 11:
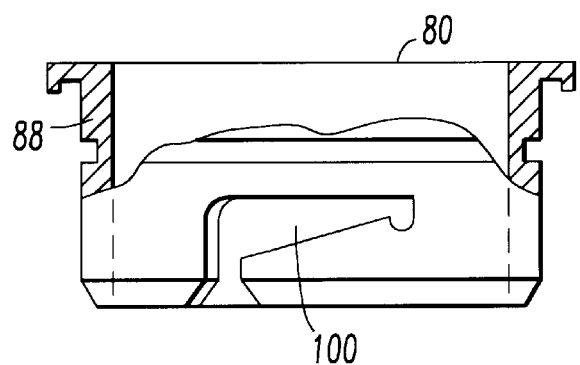
FIG. 11 is a side sectional view the quick connector shown in FIG. 10.
Figure 13:
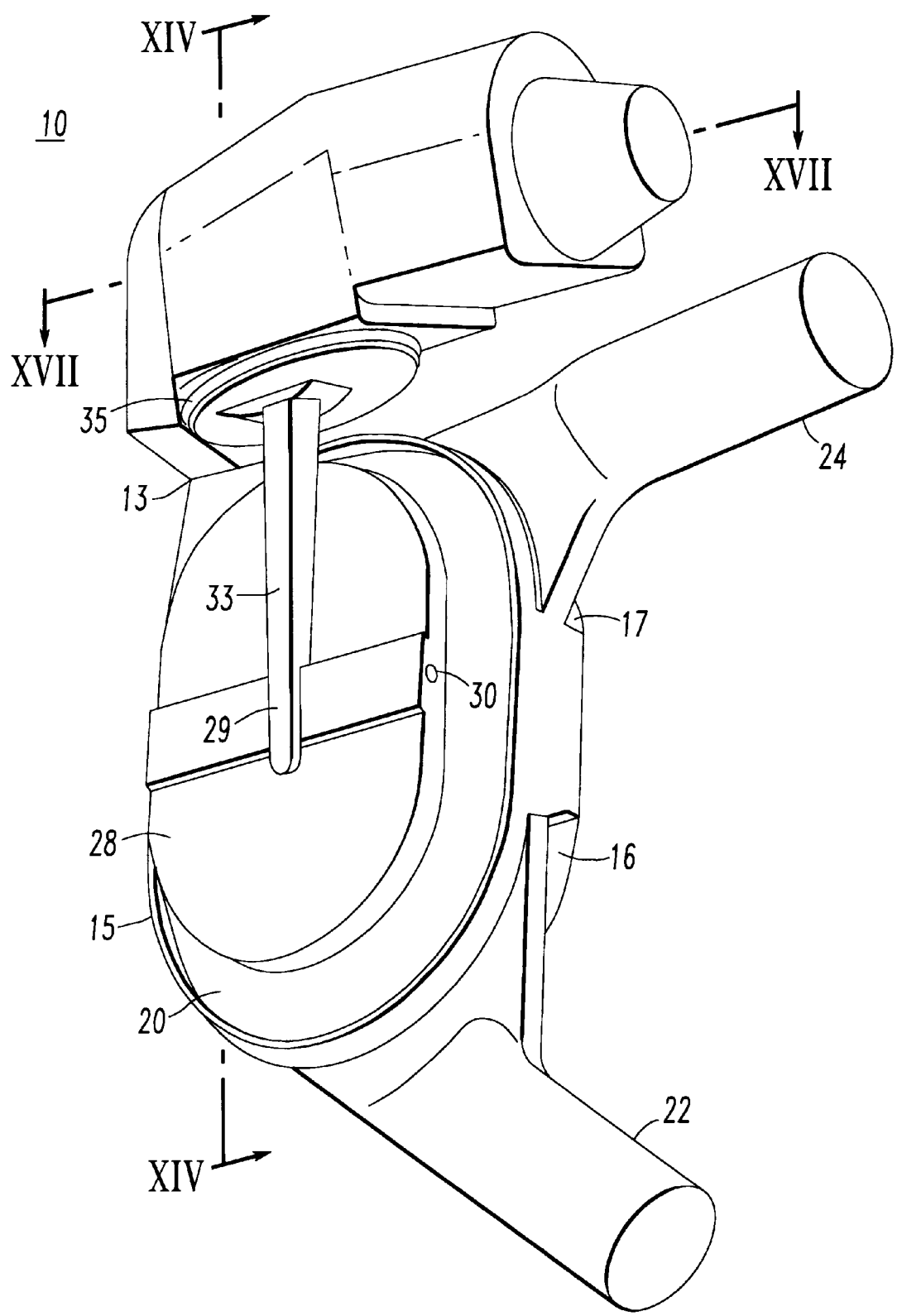
FIG. 13 is a perspective view of a blood pump apparatus.

A conventional quick-connector assembly 80 is shown in FIGS. 10 and 11. The inlet 24, or outlet 22, of the blood chamber 20 is bonded to an actuator bulkhead 84. A locking sleeve 88 can also be attached to the bulkhead 84 and can serve as the fixation point for the quick-connection portion of the quick connector 80. A vascular graft 110 can be bonded to a support ring 86. A side view, partially in section, of the locking sleeve 88 is shown in FIG. 11. A support collar 92 surrounds the support ring 86 and can have two integral locking pins 90. A compression spring 94 can be provided between the support ring 86 and the support collar 92. The spring 94 is compressed between the support ring 86 and support collar 92 and is kept in place by the locking pins 90, which can slide within a slot 98 in the support ring 86. An O-ring 82 can also be placed between the support ring 86 and support collar 92 which is kept in place by the support collar 92. Another O-ring 82 can be placed between the support collar 92 and the locking sleeve 88. In this way, the quick connector 80 can be sealed against body fluids. The actuator-end of the connector is comprised of the bulkhead 84, the inlet conduit 24 or outlet conduit 22, an O-ring 82, and the locking sleeve 88. The conduit-end of the connector is comprised of the blood flow conduit 110, the support ring 86, the locking pins 90, the support collar 92, the compression spring 94, and an O-ring 82. To assemble, the conduit-end and the actuator-end are brought together and the locking pins 90 pass through a slot 100 on the locking sleeve 88. The ends are then advanced and the support collar 92 is turned clockwise so the locking pins 90 follow the paths of the slots 100 on the locking sleeve 88. Once the connection is made, the connector's interior is sealed from body fluids by the O-rings 82 and is held in place by the locking pins 90 and the compression spring 94. It is understood that alternative quick-connector means could also be utilized. It can be important to have a quick connector means so that the delicate surgically sutured circulatory connections can be made without the physical interference of the presence of the pump. Following the suturing of the conduit-circulation connections, the surgeon can quickly attach the pump using the quick connector means.

The blood chamber 20 can be made from a resiliently compressible biostable, medical grade polyurethane such as, for example, the type of polyurethane disclosed in U.S. Pat. No. 5,133,742. Preferably, the blood-contacting interior surface of the blood chamber 20 can be integrally textured to provide a surface for tissue ingrowth to form a biologic blood-contacting surface. The texturing can consist of small fibers oriented perpendicular to the blood chamber 20 surface. Such texturing can be as disclosed in copending U.S. patent application Ser. No. 08/751,839, assigned to the assignee of the present application, and hereby incorporated herein by reference. The filamentous texture can promote the development of a biologic neointimal lining. The lining can preferably extend seamlessly throughout the blood chamber 20 and conduits 110 since the dacron grafts can also preferably develop an ingrowth of tissue resulting in a biologic surface within the graft. The blood chamber 20 can generally have a flow-through design, with minimized cross-sectional area changes in order to minimize eddies or zones of flow stagnation.

The blood chamber 20 itself is substantially lozenge-like in shape and can be formed in multiple configurations, depending on which side of the thorax the blood pump 10 is positioned and whether a serial or parallel circulation connection is chosen. By way of example, several different configurations are illustrated in FIGS. 12*a*–12*c*. In FIG. 12*a*, the blood chamber is configured for a right side parallel connection. For a left side parallel connection, the blood chamber can be a mirror image of the configuration shown in FIG. 12*a*. For a right side serial connection, the blood chamber 20 can be configured such that the inlet and outlet lie substantially opposite each other, as shown in FIG. 12*c*. However, in an alternative right side serial connection, the blood chamber 20 can be formed in a nonflow-through "blind-pouch" configuration, as shown in FIG. 12*b*. The material composition of the blood chamber 20 can be the same regardless of the particular configuration. Any configuration of the blood chamber 20 can be manufactured from the medical grade polyurethane referred to previously.

Referring now to FIGS. 13–18, wherein a blood pump apparatus according to the invention is shown having a pump housing 13 with a cupped portion 15 and a drive chamber 18, a blood chamber 20 and a drive mechanism including a pumping arm 33 and a movable plate 28. The pump housing 13, pumping arm 33 and movable plate 28 can all preferably be constructed from titanium.

The blood chamber 20 can be positioned in the cupped portion 15 of the pump housing 13. The cupped portion 15 can have openings 16, 17 for the inlet 22 and outlet 24 of the blood chamber 20. Although a cup shaped portion is shown, a generally flat base plate can also be employed. The movable plate 28, can have a shape generally corresponding to the blood chamber 20 except it can preferable have a slightly smaller area than the surface of the blood chamber 20 which the plate pushes against. Preferably, when the blood pump 10 is implanted in a patient it can be positioned such that at least a portion of the movable plate is adjacent at least a portion of the patient's lung 5. As a result, the lung 5 can move with the movable plate 28 as the plate 28 moves to pump blood, as shown in FIGS. 2*a*-2*b*. Consequently, portions of the volumetric changes in the blood pump 10 are compensated for by the lung 5 such that the lung acts as a compliance chamber for the blood pump 10.

Figure 14:
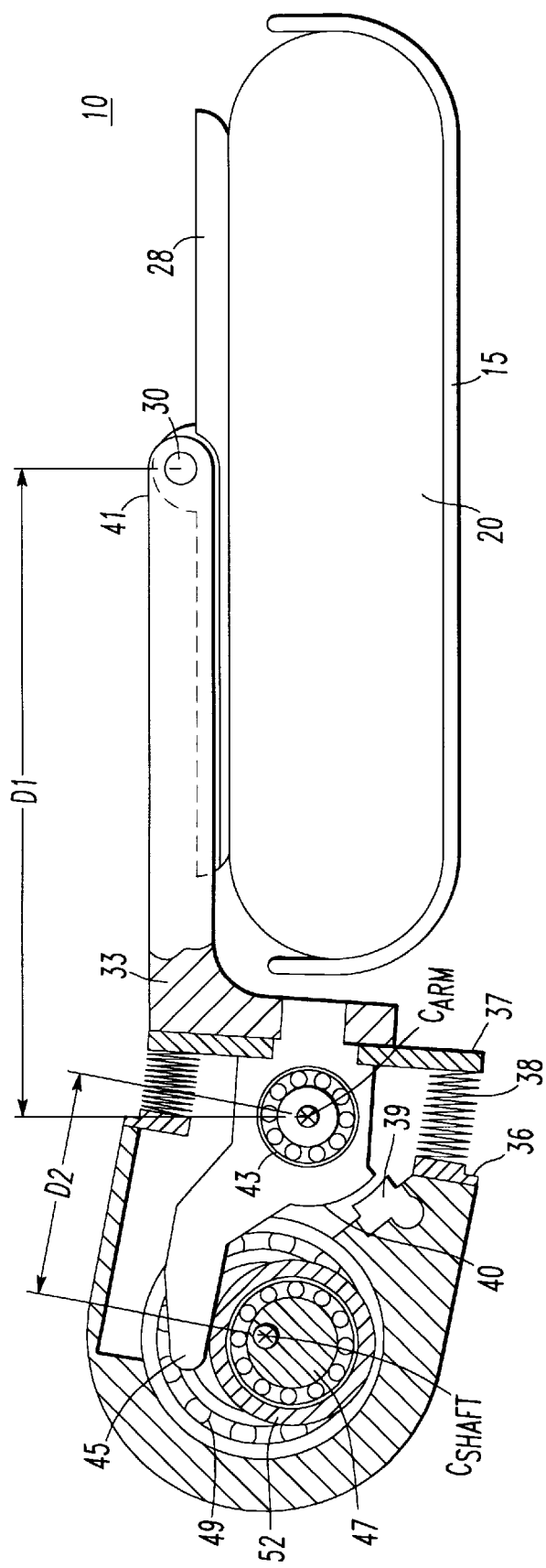
FIG. 14 is a view of the blood pump apparatus in FIG. 13 taken through line XIV—XIV.
Figure 15:
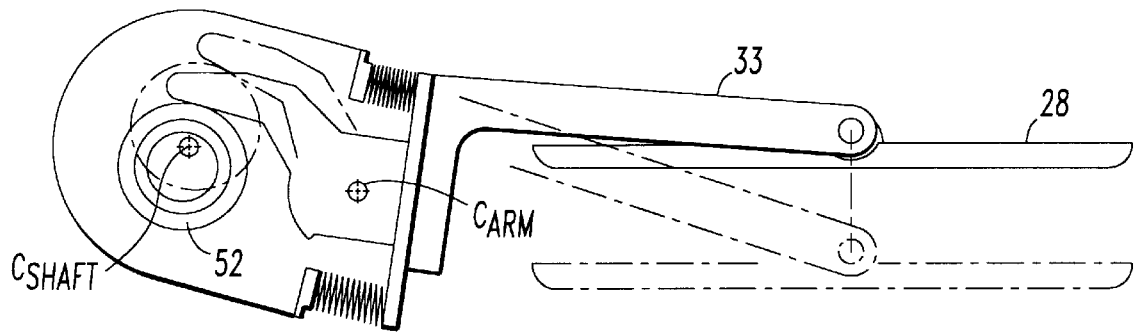
FIG. 15 illustrates translation of pivoting motion into vertical displacement.
Figure 16A:
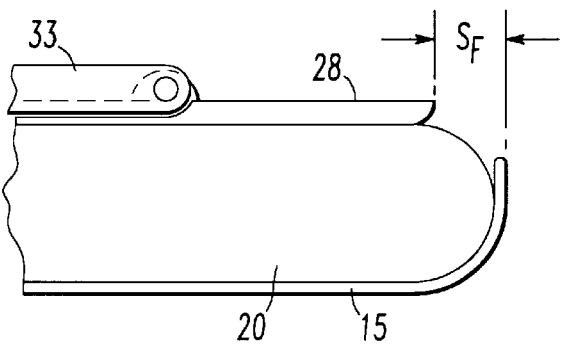
FIGS. 16a and 16b shows a how the polymeric blood chamber is pumped by the motion illustrated in FIG. 15.
Figure 16B:
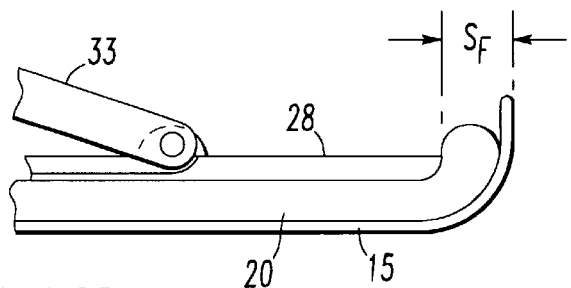

As shown in FIGS. 14 and 16*a*-16*b*, the edge of the movable plate 28 preferably is curved away from the blood chamber 20 such that when compressed, the blood chamber 20 will not have a stress concentration at the edge of the plate 28. The shape and dimensions of the blood chamber 20 and the movable plate 28 can be optimized to produce the lowest bending and hoop strains obtainable in the flexing portions of the blood chamber 20 when it is pressurized and squeezed. The blood chamber 20 should be capable of repeated deformation and still be able to return to substantially its undeformed state. Management of the bending strains can be accomplished through careful selection of the appropriate blood chamber 20 thickness so that full compression of the blood chamber 20 can be tolerated. The inlet and outlet can preferably lie within the plane of the blood chamber's 20 largest projected area. Consequently, the blood chamber 20 can have the thinnest profile.

From a theoretical standpoint, optimization of the blood chamber 20 can require consideration of a number of complex phenomena. First, the blood chamber can undergo a large amount of deflection, as depicted in FIGS. 16*a* and 16*b*. Simple strength of materials theory cannot account for this phenomenon since the components of material behavior that describe large deformation and large strain have been eliminated for simplification. As an added complication, the specific three dimensional shape of a given blood chamber 20 must be accounted for and most "text book" solutions are for simple shapes and components. Second, the polymers used in the present invention, have properties that exhibit a nonlinear relationship between stress and strain. Third, the local deformation of the blood chamber 20 as it bends around the edge of the movable plate 28 can itself be a complex contact phenomenon and is directly related to the shape of the movable plate 28 and thickness of the blood chamber 20. One practical method of evaluating the blood chamber 20, considering the aforementioned factors, can be the use of finite element analysis. This solution method breaks the component in question into many smaller and simpler pieces (elements). Each of the elements can then be solved for simultaneously and any complexities are accounted for in the element formulation. For the problem outlined above, considerable computer resources and computational time are required.

The blood chamber 20 of the present invention can simultaneously undergo bending and pressure induced strains during operation of the blood pump 10. As stated above, the bending is related to the shape of the edge of the movable plate 28 and the thickness of the blood chamber 20. The pressure strain induced by the pumping of blood is also governed by the thickness of the blood chamber 20 as well as the span $S_F$ of the bladder that is free to bear the pressure load. Essentially, the larger the span is, the greater the pressure load carried by the blood chamber 20. Increasing the thickness of the blood chamber 20 will decrease this pressure induced strain, but will increase the bending strains caused by the blood chamber 20 bending around the movable plate 28. Thus, the design problem involves balancing the bending and pressure strains. Optimization then requires that the shape of the edge of the movable plate 28, the thickness of the bladder $S_F$, and the width of the free span be varied to determine which blood chamber 20 configuration will yield the best performance.

Polymer components are typically designed to maintain a given strain level for the life of the component. Hence, it can be necessary to know the maximum strain possible for the given material and the loading frequency. Past research indicates that a maximum strain of 15% can be tolerated for 200 million cycles for the polyurethane used for this invention. Consequently, this strain level can be used as the maximum allowable strain in the design of the invention's polyurethane components.

Figure 17:
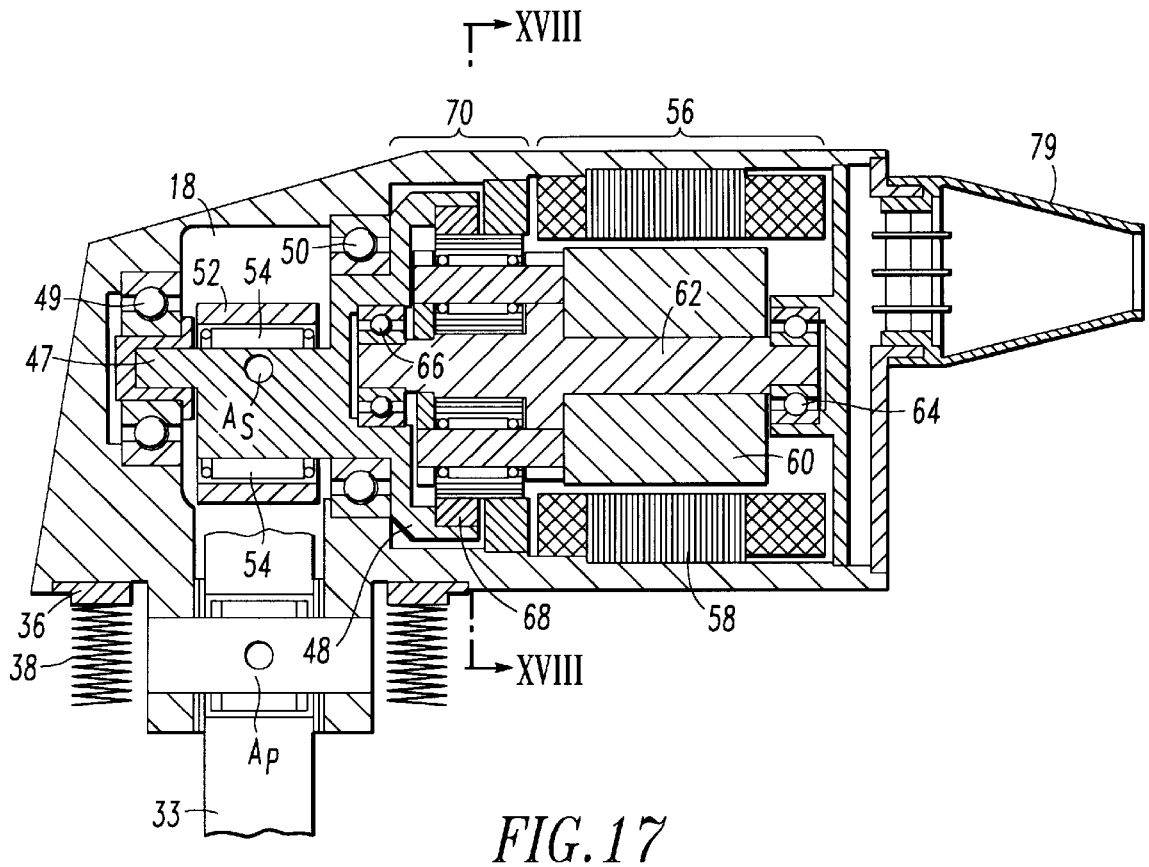
FIG. 17 is a view of the blood pump apparatus in FIG. 13 taken through line XVII—XVII.
Figure 18:
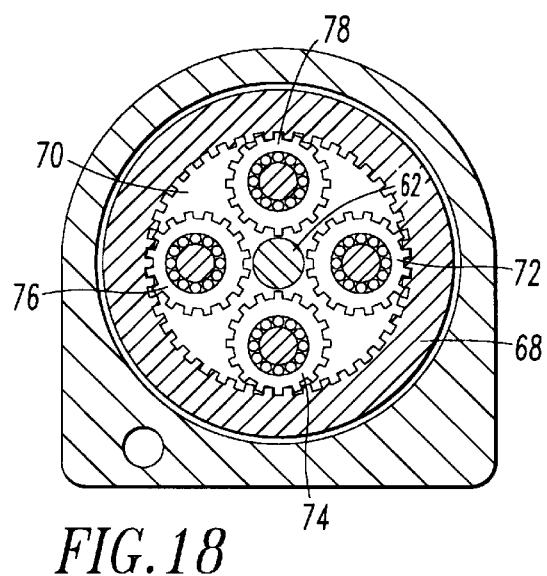
FIG. 18 is a view of the blood pump apparatus taken along line XVIII—XVIII in FIG. 17.

Referring to FIGS. 17-18, the drive mechanism can preferably include an electric servo-motor 56 coupled with a speed reducer 70 for rotating an eccentric shaft 47 which can drive the pumping arm 33 and movable plate 28 to pump blood. The servo-motor 56 can include a stator portion 58 and a rotor portion 60. The stator portion 58 can be rigidly attached to the housing and the rotor portion 60 can include an output shaft 62 for rotating the eccentric shaft 47 to operate the pumping action. A power coupling 79 can be provided to connect the servo-motor 56 to a power source and/or an EC 200. The servo-motor 56 can have various sizes or aspect ratios. The servo-motor can preferably run continuously at roughly 2,000 to 3,000 RPM. The servo-motor 56 can be, for example, manufactured by Sierracin/ Magnedyne in Carlsbad, Calif. The servo-motor 56 can preferably operate the blood pump at speeds of up to 120 beats a minute and the blood pump can have a stroke volume in the range of 60–80 ml. In addition, the blood pump must be capable of moving the stroke volume of blood against the range of arterial pressures found in humans. This level would, at generally a maximum, be around 160 mm Hg in heart failure patients. These criterion can be used to optimally design the blood chamber 20, pumping arm 33, motor 56, speed reducer 70 and other components of the blood pump apparatus 10. Further, the motor and speed reducer must be designed for quiet operation, acceptable heat generation and a long maintenance-free working life, preferably at least 5 years.

Preferably, a speed reducer 70 can be connected between the output shaft 62 and the eccentric shaft 47. The speed reducer 70 can preferably be a planetary gear reducer, shown best in FIG. 18, having a ratio of 25:1 which converts the rotary motion of the servo-motor 56 to between about 80 and 120 cycles per minutes. The servo-motor 56 speed and speed reducer 70 values can be chosen to achieve energy efficiency and provide the most compact drive mechanism. Preferably each rotation of the speed reducer's 70 output can correspond to one stroke of the blood pump 10, which occurs in the range of about 60 to 120 cycles per minute. Although commercially available speed reducers are widely available, a custom designed planetary gear reducer is preferably employed to minimize size and provide maximum efficiency. The planetary gear reducer 70 can be a three gear differential (TGD) type of speed reducer and is shown in FIG. 18. Other gear speed reduction assemblies are possible, but the TGD can be preferable because of its small size and energy efficiency, among other advantages. The gearing for this type of speed reducer 70 can include an internal ring gear 68 engaged with multiple planet gears 72, 74, 76 and 78. Internal gearing is known to have less sliding during engagement and a high contact ratio for a more gradual transfer of load. In addition, for a given size, the TGD has a higher load carrying capacity as well as longer life, higher efficiency and less noise than other types of speed reducers. The TGD employed can preferably use one less gear than the more common four gear differential, and hence can be smaller. Preferably, four planet gears can be used. This yields quadruple load paths and can have a smaller overall size than a configuration which uses fewer planets.

The output of the speed reducer can be connected to the eccentric shaft 47. As shown best in FIG. 17, the eccentric shaft 47 can have an input portion 48 which has an attached ring gear portion 68 that can be driven by the speed reducer 70. The pumping arm 33 can have a riding contact on the end of the eccentric shaft 47. Consequently, the eccentric shaft 47 can drive the pumping arm 33 during the pumping stroke yet, the pumping arm can have unrestricted, free movement during the return stoke while the blood chamber 20 is filling. Preferably, a cam, which can be a roller bearing 52 mounted on the end of the eccentric shaft 47, can be provided for the end of the pumping arm 33 to follow. The center of rotation of the eccentric shaft 47 is denoted $C_{shaft}$.

The pumping arm 33 can preferably be oriented in a plane perpendicular (orthogonally) to the spinning axis of the servo motor and speed reducer. Bearings 43 can be provided at the rotational center $C_{arm}$ of the pivotally attached intermediate portion of the pumping arm 33. A noncorroding, low wear, polymeric sleeve, not shown, may preferably be used as a bearing for connecting the pumping arm 33 to the movable plate 28. PPS sleeve material and 316L, stainless steel, for example, can be preferred materials for this joint. The end of the pumping arm that is in contact with the cam surface acts as a cam follower 45. As the cam 52 rotates on the eccentric shaft, the pumping arm 33 oscillates about its rotational center $C_{arm}$ in a cyclic rocking fashion, shown best in FIG. 15. Thus, cyclic pumping of the blood chamber 20 is accomplished. The ratio of distances from the pivoting arm's rotational center to each of its ends, denoted $D_1$ and $D_2$ in FIG. 14, determines the leverage possible with a given arm geometry. Preferably, the distance from the rotational center of the pumping arm 33 to the movable plate 28, $D_1$, can be greater than that to the cam 52 surface. The torque requirements for the eccentric shaft 47 can be considerably higher because of the pivot arm leverage. However, this can permit the energy converting hardware (servo-motor, speed reducer, and cam) to be positioned near to the rotational center $C_{shaft}$ to allow the entire drive mechanism to be more compact. Preferably, a position sensor 39 can be provided adjacent the intermediate portion of the arm 33. The sensor 39 can, for example, be an eddy current sensor for detecting changes in the position of the arm 33. The changes in the position of the arm can be used to determine a relative volume of blood in the blood chamber and also a position of the eccentric shaft 47, and the cam 52.

The movable plate 28 can have a central connection point 29 which can be the attachment location for an end 41 of the pumping arm 33. A pin 30 can be disposed through a bore in the movable plate and through a bore in the end 41 of the pusher arm 33 which thus hinges the pumping arm 33 to the movable plate 28. The to and fro rocking motion of the pumping arm 33 can preferably lie in a plane perpendicular to the movable plate 28. The hinged attachment allows the movable plate 28 to orient itself during the stroke such that the strain on the blood chamber 20 can be minimized. The rotational center $C_{arm}$ of the pumping arm 33 can preferably lie within the drive chamber.

Since the cam 52 surface provides intermittent contact with the pumping arm 33, the drive mechanism does work only during the compression phase of cam rotation and even then only to the extent that the blood chamber 20 has been filled with blood. Thus, the blood pump 10 only pumps what blood has filled the blood chamber 20 during the retracting phase of the cam surface. In this way, the movable plate 28 can be decoupled from the servo-motor while the blood chamber 20 is filling and may continue to move in an up and down fashion without pulling on the blood chamber 20. This can be very important because pulling a less than completely filled blood chamber 20 could produce undesirable wrinkling of the blood chamber membrane and/or excessively low LV pressure.

A sealing bellows 38 can preferably be provided to cover and hermetically seal the rotational center $C_{arm}$ of the pumping arm and the drive chamber 18 to keep bodily fluids away from the drive mechanism. End caps 36, 37 can be provided on either end of the sealing bellows 38. The forward end cap 37 can have an opening sealed around the pumping arm 33 where it passes through a bellows portion 35 into the drive chamber 18. The bellows 38 attaches between the end caps 36, 37 which seals the drive chamber yet can compress and expand sufficiently to either side to allow for the pivoting movement of the pumping arm 33. The bellows 38 can preferably be made from titanium. This sealing bellows 38 can be an important feature, as it allows the energy converting components to have a nonbiocompatible lubricating fluid and to shield any corrodable hard steel components from the body's salt water (saline) environment. This can greatly reduce the risk of corrosion of the gears, bearings and motor, which can result from body fluids diffusing into the drive chamber 18. The sealing bellows 38 can create a hermetic drive mechanism while still enabling the transmission of mechanical energy from the servo-motor 56 to the movable plate 28. Moreover, the hermetically sealed motor drive assembly can permit the use of hardened steel bearings, gears, and other components that can predictably operate for 5 or more years in a protected lubricated environment. The use of hardened steel components can be desirable because the rolling friction of hardened steel bearings, gears, and other motor drive components can provide highly efficient energy transfer from input electric motor power to blood work. By positioning the energy converting hardware (servo-motor, speed reducer, and cam) near to the rotational center $C_{shaft}$, the entire drive mechanism can be more compact which can minimize the motion induced in the sealing bellows. Consequently, the achievement of hermetically sealing the motor-drive mechanism is made more practical.

A polymeric enclosure bag 105, as shown in FIGS. 2a-2b, can preferably be provided around the blood pump 10 to present a friendly surface to the patient's tissue surrounding the blood pump 10. This enclosure bag 105 can preferably encompass at least the pumping arm 33 and movable plate 28 to prevent any tissue from being pinched in the area swept by the pumping arm 33. The enclosure bag 105 is preferably resiliently deformable and moves along with the movable plate 28 such that no pressure differential is created on around the enclosure bag 105. In addition, the enclosure bag 105 can prevent tissue ingrowth into this area, which could result in jamming of the pumping arm 53. Additionally, the entire blood pump 10 could be enclosed within the enclosure bag 105 if needed.

In either the parallel or serial bloodflow configuration, the blood pump 10 can operate synchronously or asynchronously with the heart 1. Synchronous operation typically means that the blood pump 10 ejects blood for each left ventricular contraction. The timing of the blood pump's ejection is governed by sensing of the hearts electrical activity (QRS), which is an indication of when the left ventricle is ejecting blood (contracting). When the electrical activity is sensed, the pump can eject immediately or after a preset delay. However, blood pump ejection preferably occurs after the left ventricle has finished its ejection. Asynchronous operation occurs when the blood pump 10 ejection frequency is independent of the hearts electrical activity (QRS). In the synchronous mode, pump contraction can be activated by, for example, the electronic controller 200 after either a programmed delay period following the sensed heart QRS signal or after a stimulating pacing pulse from the implanted electronics controller. In the asynchronous mode, pumping can be initiated by, for example, the electronic controller 200 when the position sensor 39 senses a nearly-full-blood-chamber condition.

In the asynchronous mode, it can be desirable to operate the servo-motor 56 at a relatively constant velocity to minimize reaction forces and power losses associated with acceleration and deceleration of rotating masses. The velocity can ideally be adjusted such that the blood chamber 20 is nearly filled at the beginning of each ejection phase. If the velocity is too low, the blood chamber 20 can become distended prior to the beginning of the ejection phase and limit blood inflow—potentially causing excessive left ventricular pressure. Conversely, if the velocity is too high, the volume of blood ejected from the blood chamber 20 during each cycle may be too small to adequately wash the interior surfaces of the blood chamber 20. In addition, if the velocity is too high, frictional and viscous power losses can be unnecessary high.

Figure 19:
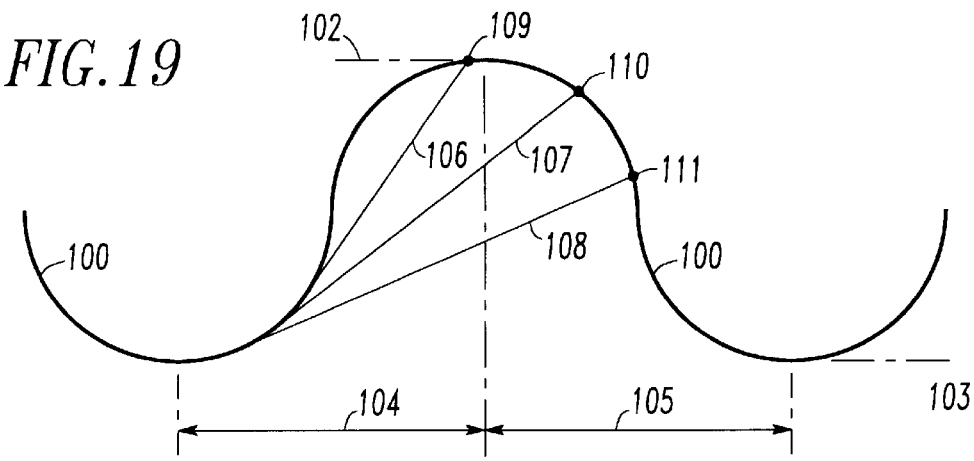
FIG. 19 is a graphic illustration of an asynchronous control method for the drive mechanism if FIG. 17.

FIG. 19 illustrates one means of optimally controlling the velocity of the motor such that the blood chamber 20 is nearly filled at the beginning of each ejection phase. Curve 100 illustrates the cyclical motion of the speed reducer output cam. At the position identified by line 102, the cam 52 is fully retracted and the pumping arm 33 is free to float as the blood chamber 20 fills to its maximally full position. At the position identified by line 103, the cam 52 is rotated 180 degrees and maximally compresses the blood chamber 20 via the pumping arm 33. The blood chamber 20 freely fills with blood flowing from the left ventricle during the inflow phase identified by line 104. During the expulsion phase identified by line 105, the blood chamber 20 is compressed by the action of the cam 52 and pumping arm 33, thereby transferring blood from the blood chamber 20 to the aorta via the outflow valve. Lines 106, 107, and 108 illustrate possible outputs of the position sensor 33 that senses the position of the pumping arm, and hence indicates the relative volume of blood in the blood chamber 20. Line 106 illustrates a scenario in which the motor velocity is too low—the blood chamber 20 completely fills prior to the beginning of ejection phase 105 and the cam 52 only begins to constrain the motion of the pumping arm 33 at point 109. Line 108 illustrates a scenario in which the motor velocity is too high—the blood chamber 20 is only partially full at the beginning of ejection phase 105 and the cam 52 only begins to constrain the motion of the pumping arm 33 at point 111. Line 107 illustrates a scenario in which the motor velocity is properly adjusted—the blood chamber 20 is nearly full at the beginning of ejection phase 105 and the cam 52 begins to constrain the motion of the pumping arm 33 shortly after the beginning of ejection phase 105 at point 110. The cam/pumping arm contact points illustrated by 109, 110 and 111 in FIG. 19 can be readily detected by identifying when the first derivative of the position sensor 39 output becomes negative. The motor velocity may be optimally adjusted by comparing the sensed cam/pumping arm contact point to an ideal contact point 110—if the contact point occurs too soon, the motor velocity is incremented, if the contact point occurs too late, the motor velocity is decremented.

In the synchronous mode, the blood chamber 20 is synchronized to the QRS signal and accepts blood during the systolic phase of LV contraction and then expels blood from the chamber during the LV diastolic phase. Conventional epicardial or endocardial ECG sensing and pacing leads can be provided between the patient and the electronic controller (EC) 200 to monitor the cardiac cycle and properly synchronize the operation of the blood pump. The period between detected QRS complexes or between pacer output pulses is used to control the velocity of the motor such that the output cam/lever makes one complete cycle per cardiac cycle. The relative phase of the motor position with respect to the detected cardiac cycle is adjusted such that the blood chamber 20 ejection phase begins approximately half way through the detected cardiac cycle when LV diastole begins.

Defibrillation electrodes can also be provided as a component of the implantable system and can be controlled by the EC 200 for the delivery of a therapy shock in the event of tachyarrhythmia or fibrillation. An implanted battery pack can also be part of the implanted system and can be capable of running the pump for several hours before needing recharging. Normally, the power for the implanted system can be obtained through transcutaneous energy and data transmission (TEDT). This can be accomplished by utilizing an implanted coil coupled with an external coil. The implanted rechargeable battery pack can be charged by the TEDT for providing power for the system when it is not being powered by the TEDT.

The electronic controller manages the operation of the motor drive based on signals received from the lever arm position sensor and any ECG sensing/pacing leads. Additional physiologic sensors can be incorporated to provide rate response heart rate control and/or AV sequential pacemaker-type control for optimizing cardiac assistance in CHF patients. Many such patients suffer chronotopic incompetence and may require rate responsive and/or AV pacing sequential control. The ECG leads can be connected to the electronic controller through a terminal block, which also serves as a connector for the defibrillation therapy leads. Operation of the electronic controller is powered by the TEDTS sub-system or, when the TEDTS sub-system is powered down, an internal battery back. The TEDTS sub-system consists of two coils, one coil is subcutaneous and the other is external to the body, an external battery pack, and a belt that holds the external battery pack and external coil against the patient's torso.

Another feature of the blood pump is the manner in which mechanical energy is converted to hemodynamic energy to accomplish the blood pumping. From a fundamental viewpoint, it can be desirable to generally minimize the number of steps required to convert the servo-motor's electrical energy to blood work. Each energy transformation has an inefficiency resulting in the loss of energy during each conversion step. In addition to minimizing the number of energy conversion steps, the efficiency of each step must be maximized.

Figure 20:
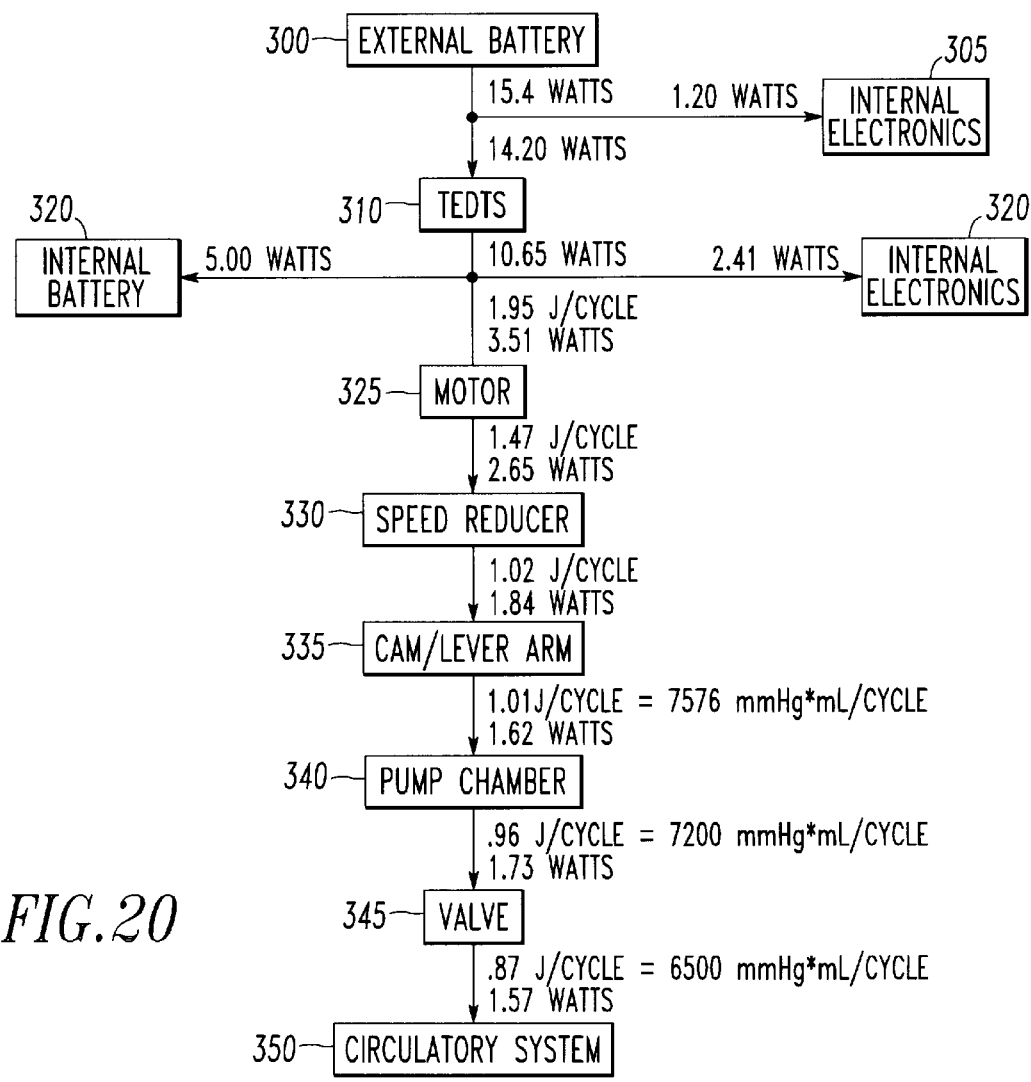
FIG. 20 is an efficiency diagram for the drive mechanism shown in FIG. 17.

A flow diagram in FIG. 20 shows the energy use and efficiencies of each component of the blood pump and associated system components. As discussed previously, each energy transfer step has an efficiency associated with it. In particular, the motor 325 has 3.51 watts supplied to it from the internal electronics 320. After passing through the energy converter, the pumping arm 33, the blood chamber 20, and any heart valve, 1.57 Watts remain to be passed through to the circulatory system 350. This translates into an efficiency of 45%, which is high for blood pumps considering that most competitive devices have efficiencies in the 10%–25% range. This higher than normal efficiency is possible due to the use of mechanical components that have their losses due to rolling friction as opposed to sliding friction. The speed reducer 330 has its main energy losses due frictional power dissipation in the bearings. Likewise, the cam/lever arm 335 dissipates power through bearings also. In addition, the hermeticity of the energy converter plays an important roll in the higher efficiencies. By isolating the energy converting hardware from the patient's body, hardened or "bearing" steels may be used which would corrode in the presence of the body's salt water environment. Components made from these materials are typically better at withstanding the wear induced from rolling friction.

Although certain embodiments of the invention have been described in detail, it will be appreciated by those skilled in the art that various modification to those details could be developed in light of the overall teaching of the disclosure. Accordingly, the particular embodiments disclosed herein are intended to be illustrative only and not limiting to the scope of the invention which should be awarded the full breadth of the following claims and any and all embodiments thereof.

What is claimed is:

1. A blood pump apparatus implantable in a patient adjacent said patient's lung for supplying blood to the patient's circulatory system, the blood pump apparatus comprising:
    a. a pump housing having a drive chamber
    b. a base connected to the pump housing;
    c. a compressible blood chamber having a first side adjacent the base, the blood chamber having an inlet and an outlet each connectable to the circulatory system;
    d. a movable portion exterior to the base and housing and adjacent a second side of the blood chamber opposite said first side, said movable portion positionable adjacent a portion of said lung such that as the blood is pumped portions of volumetric changes in the compressible blood chamber are compensated for during movement of said movable portion;
    e. an arm having a first end pivotably connected to the movable portion; and
    f. a drive mechanism housed in the drive chamber and connected to a second end of the arm, wherein the drive mechanism operates the arm to compress the blood chamber between the movable portion and the base to pump blood through the circulatory system.

2. The blood pump of claim 1 wherein the drive mechanism further comprises:
    a. an eccentric shaft having an input end and an output end;
    b. the arm having a second end movable by the output end of the eccentric shaft; and
    c. a motor housed in the drive chamber, the motor having an output shaft connected to the input end of the eccentric shaft for rotating the eccentric shaft thereby causing the arm to operate the movable portion to compress and release the blood chamber to pump blood through the circulatory system.

3. The blood pump of claim 2 further comprising a speed reducer connected intermediate the output shaft of the motor and the input end of the eccentric shaft.

4. The blood pump of claim 2 wherein the arm is mounted in a plane orthogonal to an axis of rotation of the eccentric shaft.

5. The blood pump of claim 1 further comprising a position sensor disposed in the drive chamber for detecting changes in the position of the arm to determine at least one of a volume of blood in the blood chamber and a position of the eccentric shaft.

6. The blood pump of claim 5 further comprising the position sensor disposed adjacent an intermediate point of the arm for detecting changes in the angle of the arm.

7. The blood pump of claim 6 wherein the position sensor comprises an eddy current sensor.

8. The blood pump of claim 6 wherein the bellows is hermetically sealed.

9. The blood pump according to claim 1 further comprising a bellows member sealing an end of the drive chamber and around the second end of the arm, the bellows permitting pivotal movement of the arm while preventing bodily fluids from entering into the drive chamber.

10. The blood pump of claim 1 further comprising an implantable electronic controller operatively connected to and controlling the drive mechanism.

11. The blood pump of claim 1 further comprising the compressible blood chamber having a textured inner surface for promoting the development of a biologic neointimal lining.

12. A blood pump apparatus implantable in a patient for supplying blood to the patient's circulatory system, the blood pump apparatus comprising:

a. a pump housing having a drive chamber
   b. a base connected to the pump housing;
   c. a compressible blood chamber having a first side adjacent the base, the blood chamber having an inlet and an outlet each connectable to the circulatory system;
   d. a movable portion adjacent a second side of the blood chamber opposite the base, at least a portion of the movable portion positionable adjacent a portion of a lung such that the movement of the movable portion is opposed by the lung as the blood is pumped whereby portions of volumetric changes in the compressible blood chamber are compensated for by the lung;
   e. an arm having a first end pivotably connected to the movable portion;
   f. a drive mechanism housed in the drive chamber and connected to a second end of the arm, wherein the drive mechanism operates the arm to compress the blood chamber between the movable portion and the base to pump blood through the circulatory system;
   g. an eccentric shaft having an input end and an output end;
   h. the arm having a second end movable by the output end of the eccentric shaft;
   i. a motor housed in the drive chamber, the motor having an output shaft connected to the input end of the eccentric shaft for rotating the eccentric shaft thereby causing the arm to operate the movable portion to compress and release the blood chamber to pump blood through the circulatory system; and
   j. the second end of the arm having riding contact with the output end of the eccentric shaft, the eccentric shaft driving the arm during a pumping stroke and the arm having unrestricted movement during a return stroke.

13. The blood pump of claim 12 further comprising a roller bearing mounted on the output end of the eccentric shaft whereon the arm has riding contact on the roller bearing.

14. A blood pump apparatus implantable in a patient for supplying blood to the patient's circulatory system, the blood pump apparatus comprising:

a. a pump housing having a drive chamber
   b. a base connected to the pump housing;
   c. a compressible blood chamber having a first side adjacent the base, the blood chamber having an inlet and an outlet each connectable to the circulatory system;
   d. a movable portion adjacent a second side of the blood chamber opposite the base, at least a portion of the movable portion positionable adjacent a portion of a lung such that the movement of the movable portion is opposed by the lung as the blood is pumped whereby portions of volumetric changes in the compressible blood chamber are compensated for by the lung;
   e. an arm having a first end pivotably connected to the movable portion;
   f. a drive mechanism housed in the drive chamber and connected to a second end of the arm, wherein the drive mechanism operates the arm to compress the blood chamber between the movable portion and the base to pump blood through the circulatory system;
   g. an eccentric shaft having an input end and an output end;
   h. the arm having a second end movable by the output end of the eccentric shaft;
   i. a motor housed in the drive chamber, the motor having an output shaft connected to the input end of the eccentric shaft for rotating the eccentric shaft thereby causing the arm to operate the movable portion to compress and release the blood chamber to pump blood through the circulatory system;
   j. a speed reducer connected intermediate the output shaft of the motor and the input end of the eccentric shaft; and
   k. wherein the speed reducer comprises a planetary gear reducer.

15. The blood pump of claim 14 wherein the planetary gear reducer is a three gear differential type speed reducer.

16. The blood pump of claim 15 wherein the planetary gear reducer has an internal ring gear.

17. The blood pump of claim 16 wherein the planetary gear reducer has four planet gears engaged with said internal ring gear.

18. A blood pump apparatus implantable in a patient for supplying blood to the patient's circulatory system, the blood pump apparatus comprising:

a. a pump housing having a drive chamber
   b. a base connected to the pump housing;
   c. a compressible blood chamber having a first side adjacent the base, the blood chamber having an inlet and an outlet each connectable to the circulatory system;
   d. a movable portion adjacent a second side of the blood chamber opposite the base, at least a portion of the movable portion positionable adjacent a portion of a lung such that the movement of the movable portion is opposed by the lung as the blood is pumped whereby portions of volumetric changes in the compressible blood chamber are compensated for by the lung;
   e. an arm having a first end pivotably connected to the movable portion;
   f. a drive mechanism housed in the drive chamber and connected to a second end of the arm, wherein the drive mechanism operates the arm to compress the blood chamber between the movable portion and the base to pump blood through the circulatory system; and
   g. an enclosure bag surrounding the blood pump and having a sealable opening for at least the inlet and the outlet of the blood chamber wherein the enclosure bag provides a tissue friendly surface and prevents such tissue from becoming caught between any moving parts of the blood pump.

19. The blood pump of claim 18 wherein the enclosure bag is deformable such that there is no pressure differential surrounding the bag.

20. A blood pump apparatus implantable in a patient for supplying blood to the patient's circulatory system, the blood pump apparatus comprising:

a. a pump housing having a drive portion and a pump portion;
   b. a compressible blood chamber disposed in the pump portion, the blood chamber having an inlet and an outlet each connectable to the circulatory system;

c. at least one movable portion exterior to the base and housing and adjacent at least one side of the blood chamber for compressing the blood chamber to pump blood, at least a portion of the at least one movable portion positionable adjacent a portion of a lung such that the movement of the at least one movable portion is opposed by the lung as the blood is pumped whereby portions of volumetric changes in the compressible blood chamber are compensated for by the lung;

d. at least one arm having a first end and an intermediate portion, the first end pivotably connected to the at least one movable portion and the intermediate portion pivotably connected to the housing;

e. an eccentric shaft having an input end and an output end;

f. the arm having a second end movable by the output end of the eccentric shaft; and g. a motor housed in the drive chamber, the motor having an output shaft connected to the input end of the eccentric shaft for rotating the eccentric shaft thereby causing the arm to operate the at least one movable portion to compress the blood chamber to pump blood through the circulatory system.

21. The blood pump of claim 20 further comprising a speed reducer connected intermediate the output shaft of the motor and the input end of the eccentric shaft.

22. The blood pump of claim 20 wherein the arm is mounted in a plane orthogonal to an axis of rotation of the eccentric shaft.

23. The blood pump of claim 20 further comprising a position sensor disposed in the drive portion for detecting changes in the position of the arm to determine at least one of a volume of blood in the blood chamber and a position of the eccentric shaft.

24. The blood pump of claim 23 further comprising the position sensor disposed adjacent an intermediate point of the arm for detecting changes in the angle of the arm.

25. The blood pump of claim 24 wherein the position sensor comprises an eddy current sensor.

26. The blood pump according to claim 20 further comprising a bellows member sealing an end of the drive portion and around the intermediate portion of the arm, the bellows permitting pivotal movement of the arm while preventing bodily fluids from entering into the drive chamber.

27. The blood pump of claim 26 wherein the bellows is hermetically sealed.

28. The blood pump of claim 20 further comprising an implantable electronic controller operatively connected to and controlling the motor.

29. The blood pump of claim 20 further comprising the compressible blood chamber having a textured inner surface for promoting the development of a biologic neointimal lining.

30. A blood pump apparatus implantable in a patient for supplying blood to the patient's circulatory system, the blood pump apparatus comprising:

a. a pump housing having a drive portion and a pump portion;

b. a compressible blood chamber disposed in the pump portion, the blood chamber having an inlet and an outlet each connectable to the circulatory system;

c. at least one movable portion adjacent at least one side of the blood chamber for compressing the blood chamber to pump blood;

d. at least one arm having a first end and an intermediate portion, the first end pivotably connected to the at least one movable portion and the intermediate portion pivotably connected to the housing;

e. an eccentric shaft having an input end and an output end;

f. the arm having a second end movable by the output end of the eccentric shaft;

g. a motor housed in the drive portion, the motor having an output shaft connected to the input end of the eccentric shaft for rotating the eccentric shaft thereby causing the arm to operate the at least one movable portion to compress the blood chamber to pump blood through the circulatory system; and h. the second end of the arm having riding contact with the output end of the eccentric shaft, the eccentric shaft driving the arm during a pumping stroke and the arm having unrestricted movement during a return stroke.

31. The blood pump of claim 30 further comprising a roller bearing mounted on the end of the eccentric shaft whereon the arm has riding contact.

32. A blood pump apparatus implantable in a patient for supplying blood to the patient's circulatory system, the blood pump apparatus comprising:

a. a pump housing having a drive portion and a pump portion;

b. a compressible blood chamber disposed in the pump portion, the blood chamber having an inlet and an outlet each connectable to the circulatory system;

c. at least one movable portion adjacent at least one side of the blood chamber for compressing the blood chamber to pump blood;

d. at least one arm having a first end and an intermediate portion, the first end pivotably connected to the at least one movable portion and the intermediate portion pivotably connected to the housing;

e. an eccentric shaft having an input end and an output end;

f. the arm having a second end movable by the output end of the eccentric shaft;

g. a motor housed in the drive portion the motor having an output shaft connected to the input end of the eccentric shaft for rotating the eccentric shaft thereby causing the arm to operate the at least one movable portion to compress the blood chamber to pump blood through the circulatory system;

h. a speed reducer connected intermediate the output shaft of the motor and the input end of the eccentric shaft; and i. wherein the speed reducer comprises a planetary gear reducer.

33. The blood pump of claim 32 wherein the planetary gear reducer is a three gear differential type speed reducer.

34. The blood pump of claim 33 wherein the planetary gear reducer has an internal ring gear.

35. The blood pump of claim 34 wherein the planetary gear reducer has four planet gears engaged with said internal ring gear.

36. A blood pump apparatus implantable in a patient for supplying blood to the patient's circulatory system, the blood pump apparatus comprising:

a. a pump housing having a drive portion and a pump portion;

b. a compressible blood chamber disposed in the pump portion, the blood chamber having an inlet and an outlet each connectable to the circulatory system;

c. at least one movable portion adjacent at least one side of the blood chamber for compressing the blood chamber to pump blood;

d. at least one arm having a first end and an intermediate portion, the first end pivotably connected to the at least one movable portion and the intermediate portion pivotably connected to the housing;

e. an eccentric shaft having an input end and an output end;

f. the arm having a second end movable by the output end of the eccentric shaft;

g. a motor housed in the drive portion, the motor having an output shaft connected to the input end of the eccentric shaft for rotating the eccentric shaft thereby causing the arm to operate the at least one movable portion to compress the blood chamber to pump blood through the circulatory system; and h. an enclosure bag surrounding the blood pump and having a sealable opening for at least the inlet and the outlet of the blood chamber wherein the enclosure bag provides a tissue friendly surface and prevents such tissue from becoming caught between any moving parts of the blood pump.

37. The blood pump of claim 36 wherein the enclosure bag is deformable such that there is no pressure differential surrounding the bag.

38. A blood pump apparatus implantable in a patient for supplying blood to the patient's circulatory system, the blood pump apparatus comprising:

a. a pump housing having a drive portion and a pump portion;

b. a compressible blood chamber disposed in the pump portion, the blood chamber having an inlet and an outlet each connectable to the circulatory system;

c. at least one movable portion adjacent at least one side of the blood chamber for compressing the blood chamber to pump blood;

d. at least one arm having a first end connected to the at least one movable portion and an intermediate portion pivotably connected to the housing;

e. a drive mechanism housed in the drive portion and connected to a second end of the at least one arm wherein the drive mechanism causes the at least one arm to pivot about the intermediate portion to cause the at least one movable portion to compress the blood chamber to pump blood through the circulatory system; and f. a bellows member sealing an end of the drive portion and around the second end of the at least one arm, the bellows permitting pivotal movement of the at least one arm while preventing bodily fluids from entering into the drive portion.

39. The blood pump of claim 38 wherein the bellows is hermetically sealed.

40. The blood pump of claim 38 wherein the drive mechanism further comprises:

a. an eccentric shaft having an input end and an output end;

b. the at least one arm having a second end movable by the output end of the eccentric shaft; and c. a motor housed in the drive chamber, the motor having an output shaft connected to the input end of the eccentric shaft for rotating the eccentric shaft thereby causing the at least one arm to operate the at least one movable portion to compress the blood chamber to pump blood through the circulatory system.

41. The blood pump of claim 40 further comprising the second end of the at least one arm having riding contact with the output end of the eccentric shaft, the eccentric shaft driving the at least one arm during a pumping stroke and the at least one arm having unrestricted movement during a return stroke.

42. The blood pump of claim 41 further comprising a roller bearing mounted on the output end of the eccentric shaft whereon the at least one arm has riding contact on the roller bearing.

43. The blood pump of claim 40 further comprising a speed reducer connected intermediate the output shaft of the motor and the opposite end of the eccentric shaft.

44. The blood pump of claim 43 wherein the speed reducer comprises a planetary gear reducer.

45. The blood pump of claim 44 wherein the planetary gear reducer is a three gear differential type speed reducer.

46. The blood pump of claim 45 wherein the planetary gear reducer has an internal ring gear.

47. The blood pump of claim 46 wherein the planetary gear reducer has four planet gears engaged with said internal ring gear.

48. The blood pump of claim 40 wherein the arm is mounted in a plane orthogonal to an axis of rotation of the eccentric shaft.

49. The blood pump of claim 38 further comprising a position sensor disposed in the drive portion for detecting changes in the position of the at least one arm to determine at least one of a volume of blood in the blood chamber and a position of the eccentric shaft.

50. The blood pump of claim 49 further comprising the position sensor disposed adjacent an intermediate point of the at least one arm for detecting changes in the angle of the at least one arm.

51. The blood pump of claim 50 wherein the position sensor comprises an eddy current sensor.

52. The blood pump of claim 38 further comprising an implantable electronic controller operatively connected to and controlling the drive mechanism.

53. The blood pump of claim 38 further comprising an enclosure bag surrounding the blood pump and having a sealable opening for at least the inlet and the outlet of the blood chamber wherein the enclosure bag provides a tissue friendly surface and prevents such tissue from becoming caught between any moving parts of the blood pump.

54. The blood pump of claim 53 wherein the enclosure bag is deformable such that there is no pressure differential surrounding the bag.

55. The blood pump of claim 38 further comprising the compressible blood chamber having a textured inner surface for promoting the development of a biologic neointimal lining.

56. A blood pump apparatus implantable in a patient adjacent said patient's lung for supplying blood to said patient's circulatory system, said blood pump apparatus comprising:

a. a pump housing having a drive chamber b. a base connected to the pump housing;

c. a compressible blood chamber having a first side adjacent said base, said blood chamber having an inlet and an outlet each connectable to said circulatory system;

d. a movable portion exterior to said base and housing and adjacent a second side of said blood chamber opposite said first side, said movable portion positionable adjacent a portion of said lung such that as the blood is pumped portions of volumetric changes in said compressible blood chamber are compensated for during movement of said movable portion; and e. a drive mechanism housed in said drive chamber and connected to said movable portion, said drive mechanism operating said movable portion to compress said blood chamber between said movable portion and said base to pump blood through said circulatory system.

* * * * *